US009701718B2

(12) United States Patent
Sullivan et al.

(10) Patent No.: US 9,701,718 B2
(45) Date of Patent: Jul. 11, 2017

(54) ADENOVIRUS SEROTYPE 26 AND SEROTYPE 35 FILOVIRUS VACCINES

(75) Inventors: Nancy J. Sullivan, Kensington, MD (US); Gary J. Nabel, Washington, DC (US); Clement Asiedu, Olney, MD (US); Cheng Cheng, Rockville, MD (US); Maria Grazia Pau, Leiden (NL); Jaap Goudsmit, Amsterdam (NL)

(73) Assignees: Janssen Vaccines & Prevention B.V., Leiden (NL); THE UNITED STATES OF AMERICA, AS REPRESENTED BY THE SECRETARY, DEPARTMENT OF HEALTH AND HUMAN SERVICES, THE OFFICE OF TECHNOLOGY TRANSFER, NATIONAL INSTITUTE OF HEALTH, Washington, DC (US)

( * ) Notice: Subject to any disclaimer, the term of this patent is extended or adjusted under 35 U.S.C. 154(b) by 0 days.

(21) Appl. No.: 13/994,532

(22) PCT Filed: Dec. 14, 2011

(86) PCT No.: PCT/US2011/064944
§ 371 (c)(1),
(2), (4) Date: Sep. 30, 2013

(87) PCT Pub. No.: WO2012/082918
PCT Pub. Date: Jun. 21, 2012

(65) Prior Publication Data

US 2014/0017278 A1 Jan. 16, 2014

Related U.S. Application Data

(60) Provisional application No. 61/422,954, filed on Dec. 14, 2010.

(51) Int. Cl.
*C07K 14/005* (2006.01)
*A61K 39/00* (2006.01)
*A61K 39/12* (2006.01)

(52) U.S. Cl.
CPC ............ *C07K 14/005* (2013.01); *A61K 39/12* (2013.01); *A61K 2039/5254* (2013.01); *A61K 2039/5256* (2013.01); *A61K 2039/70* (2013.01); *C12N 2710/10034* (2013.01); *C12N 2710/10043* (2013.01); *C12N 2760/14034* (2013.01); *C12N 2760/14134* (2013.01)

(58) Field of Classification Search
CPC ...... A61K 39/12; A61K 2039/53; C12N 7/00; C12N 15/86; C12N 2320/31; C12N 2710/10034; C07K 14/005; C07K 14/08
See application file for complete search history.

(56) References Cited

U.S. PATENT DOCUMENTS

| | | | | |
|---|---|---|---|---|
| 6,852,324 B1 * | 2/2005 | Nabel | C07K 14/005 | 424/199.1 |
| 7,094,598 B2 * | 8/2006 | Nabel et al. | 435/320.1 | |
| 7,635,485 B2 * | 12/2009 | Nabel | A61K 39/12 | 424/199.1 |
| 7,635,688 B2 * | 12/2009 | Nabel | C07K 14/005 | 424/9.2 |
| 7,741,099 B2 | 6/2010 | Havenga et al. | | |
| 8,017,130 B2 * | 9/2011 | Nabel | A61K 39/12 | 424/199.1 |
| 8,101,739 B2 | 1/2012 | Sullivan et al. | | |
| 8,106,026 B2 * | 1/2012 | Nabel | C07K 14/005 | 424/9.2 |
| 8,106,027 B2 * | 1/2012 | Nabel | C07K 14/005 | 424/9.2 |
| 8,124,592 B2 * | 2/2012 | Nabel | C07K 14/005 | 424/9.2 |
| 2004/0259825 A1 | 12/2004 | Nabel et al. | | |
| 2005/0196384 A1 * | 9/2005 | Vogels et al. | 424/93.2 | |
| 2006/0148087 A1 | 7/2006 | Nabel et al. | | |
| 2008/0199939 A1 | 8/2008 | Havenga et al. | | |
| 2009/0110695 A1 * | 4/2009 | Havenga | A61K 39/235 | 424/199.1 |
| 2009/0232841 A1 | 9/2009 | Sullivan et al. | | |
| 2010/0015176 A1 * | 1/2010 | Vogels | C07K 14/005 | 424/199.1 |
| 2010/0297171 A1 | 11/2010 | Nabel et al. | | |
| 2010/0298414 A1 | 11/2010 | Nabel et al. | | |
| 2010/0303857 A1 * | 12/2010 | Nabel | C07K 14/005 | 424/204.1 |
| 2011/0311580 A1 * | 12/2011 | Vogels | C07K 14/005 | 424/199.1 |
| 2012/0156239 A1 * | 6/2012 | Sullivan et al. | 424/204.1 | |

FOREIGN PATENT DOCUMENTS

| | | |
|---|---|---|
| WO | 03028632 A2 | 4/2003 |
| WO | 03104467 A1 | 12/2003 |
| WO | 04001032 A2 | 12/2003 |
| WO | 2006037038 A1 | 4/2006 |
| WO | 2006040330 A2 | 4/2006 |
| WO | 2007104792 A2 | 9/2007 |
| WO | 2012082918 A1 | 6/2012 |

OTHER PUBLICATIONS

Ledgerwood JE, et. al.; VRC 205 Study Team. A replication defective recombinant Ad5 vaccine expressing Ebola virus GP is safe and immunogenic in healthy adults. Vaccine. Dec. 16, 2010;29(2):304-13. Epub Oct. 27, 2010.*
Geisbert TW, et. al. Recombinant adenovirus serotype 26 (Ad26) and Ad35 vaccine vectors bypass immunity to Ad5 and protect nonhuman primates against ebolavirus challenge. J Virol. May 2011;85(9):4222-33. Epub Feb. 16, 2011.*

(Continued)

*Primary Examiner* — Rachel B Gill
(74) *Attorney, Agent, or Firm* — Panitch Schwarze Belisario & Nadel LLP

(57) ABSTRACT

Provided are recombinant adenovirus vectors (serotype 26 and serotype 35) encoding filovirus antigens. The adenovirus vectors can be used to induce protective immune responses against filovirus infection.

15 Claims, 6 Drawing Sheets

(56) References Cited

OTHER PUBLICATIONS

Wang D, Raja NU, Trubey CM, Juompan LY, Luo M, Woraratanadharm J, Deitz SB, Yu H, Swain BM, Moore KM, Pratt WD, Hart MK, Dong JY. Development of a cAdVax-based bivalent ebola virus vaccine that induces immune responses against both the *Sudan* and *Zaire* species of Ebola virus. J Virol. Mar. 2006;80(6):2738-46.*

Richardson JS, Yao MK, Tran KN, Croyle MA, Strong JE, Feldmann H, Kobinger GP. Enhanced protection against Ebola virus mediated by an improved adenovirus-based vaccine. PLoS One. 2009;4(4):e5308. Epub Apr. 23, 2009.*

PCT International Search Report, PCT/US2011/064944, dated Feb. 28, 2012.

Geisbert, et al., Recombinant Adenovirus Serotype 26 (AD26) and Ad35) Vaccine Vectors Bypass Immunity to Ad5 and Protect Nonhuman Primates against Ebolavirus Challenge, Journal of Virology, pp. 4222-4233, vol. 85, No. 9.

Zahn et al., Ad35 and Ad26 Vaccine Vectors Induce Potent and Cross-Reactive Antibody and T-Cell Responses to Multiple *Filovirus* Species, PLOS-One, Dec. 2012, e44115, vol. 7, No. 12.

Lemckert et al., Immunogenicity of Heterologous Prime-Boost Regimens Involving Recombinant Adenovirus Serotype 11 (Ad11) and Ad35 Vaccine Vectors in the Presence of Anti-Ad5 Immunity, Journal of Virology, Jul. 2005, p. 9694-701, vol. 79, No. 15, American Society for Microbiology.

Thorner et al., Immunogenicity of Heterologous Recombinant Adenovirus Prime-Boost Vaccine Regimens is Enhanced by Circumverting Vector Cross-Reactivity, Journal of Virology, Dec. 2006, pp. 12009-12016, vol. 80, No. 24, American Society for Microbiology.

* cited by examiner

A

B

SEQUENCE LISTING

```
<160> NUMBER OF SEQ ID NOS: 4

<210> SEQ ID NO 1
<211> LENGTH: 2302
<212> TYPE: DNA
<213> ORGANISM: Ebola virus
<220> FEATURE:
<223> OTHER INFORMATION: Ebola virus (EBOV) transmembrane envelope
      glycoprotein (GP) Zaire type species (ZEBOV) wild type filovirus
      antigen
```

-continued

<400> SEQUENCE: 1

```
cgtcgtcgac acgtgtgatc agatatcgcg gccgctctag accaggccct ggatcgatcc      60
aacaacacaa tgggcgttac aggaatattg cagttacctc gtgatcgatt caagaggaca     120
tcattctttc tttgggtaat tatccttttc caaagaacat tttccatccc acttggagtc     180
atccacaata gcacattaca ggttagtgat gtcgacaaac tagtttgtcg tgacaaactg     240
tcatccacaa atcaattgag atcagttgga ctgaatctcg aagggaatgg agtggcaact     300
gacgtgccat ctgcaactaa aagatggggc ttcaggtccg gtgtcccacc aaaggtggtc     360
aattatgaag ctggtgaatg ggctgaaaac tgctacaatc ttgaaatcaa aaaacctgac     420
gggagtgagt gtctaccagc agcgccagac gggattcggg gcttcccccg gtgccggtat     480
gtgcacaaag tatcaggaac gggaccgtgt gccggagact ttgccttcca taaagagggt     540
gctttcttcc tgtatgatcg acttgcttcc acagttatct accgaggaac gactttcgct     600
gaaggtgtcg ttgcatttct gatactgccc caagctaaga aggacttctt cagctcacac     660
cccttgagag agccggtcaa tgcaacggag gacccgtcta gtggctacta ttctaccaca     720
attagatatc aggctaccgg ttttggaacc aatgagacag agtacttgtt cgaggttgac     780
aatttgacct acgtccaact tgaatcaaga ttcacaccac agtttctgct ccagctgaat     840
gagacaatat atacaagtgg gaaaaggagc aataccacgg gaaaactaat ttggaaggtc     900
aaccccgaaa ttgatacaac aatcggggag tgggccttct gggaaactaa aaaaaacctc     960
actagaaaaa ttcgcagtga agagttgtct ttcacagttg tatcaaacgg agccaaaaac    1020
atcagtggtc agagtccggc gcgaacttct tccgacccag ggaccaacac aacaactgaa    1080
gaccacaaaa tcatggcttc agaaaattcc tctgcaatgg ttcaagtgca cagtcaagga    1140
agggaagctg cagtgtcgca tctaacaacc cttgccacaa tctccacgag tccccaatcc    1200
ctcacaacca aaccaggtcc ggacaacagc acccataata cacccgtgta taaacttgac    1260
atctctgagg caactcaagt tgaacaacat caccgcagaa cagacaacga cagcacagcc    1320
tccgacactc cctctgccac gaccgcagcc ggacccccaa aagcagagaa caccaacacg    1380
agcaagagca ctgacttcct ggaccccgcc accacaacaa gtccccaaaa ccacagcgag    1440
accgctggca acaacaacac tcatcaccaa gataccggag aagagagtgc cagcagcggg    1500
aagctaggct taattaccaa tactattgct ggagtcgcag gactgatcac aggcgggaga    1560
agaactcgaa gagaagcaat tgtcaatgct caacccaaat gcaaccctaa tttacattac    1620
tggactactc aggatgaagg tgctgcaatc ggactggcct ggataccata tttcgggcca    1680
gcagccgagg gaatttacat agaggggcta atgcacaatc aagatggttt aatctgtggg    1740
ttgagacagc tggccaacga gacgactcaa gctcttcaac tgttcctgag agccacaact    1800
gagctacgca ccttttcaat cctcaaccgt aaggcaattg atttcttgct gcagcgatgg    1860
ggcggcacat gccacattct gggaccggac tgctgtatcg aaccacatga ttggaccaag    1920
aacataacag acaaaattga tcagattatt catgattttg ttgataaaac ccttccggac    1980
caggggggaca atgacaattg gtggacagga tggagacaat ggataccggc aggtattgga    2040
gttacaggcg ttgtaattgc agttatcgct ttattctgta tatgcaaatt tgtcttttag    2100
tttttcttca gattgcttca tggaaaagct cagcctcaaa tcaatgaaac caggatttaa    2160
ttatatggat tacttgaatc taagattact tgacaaatga taatataata cactggagct    2220
ttaaacatag ccaatgtgat tctaactcct ttaaactcac agttaatcat aaacaaggtt    2280
tgaggtaccg agctcgaatt ga                                             2302
```

-continued

<210> SEQ ID NO 2
<211> LENGTH: 2031
<212> TYPE: DNA
<213> ORGANISM: Artificial Sequence
<220> FEATURE:
<223> OTHER INFORMATION: synthetic Ebola virus (EBOV) transmembrane envelope glycoprotein (GP) Sudan/Gulu type species (SEBOV) codon optimized filovirus antigen

<400> SEQUENCE: 2

```
atggagggcc tgagcctgct gcagctgccc agggacaagt tcaggaagag cagcttcttc     60

gtgtgggtga tcatcctgtt ccagaaggcc ttcagcatgc ccctgggcgt ggtgaccaac    120

agcaccctgg aggtgaccga gatcgaccag ctggtgtgca aggaccacct ggccagcacc    180

gaccagctga agagcgtggg cctgaacctg gagggcagcg gcgtgagcac cgacatcccc    240

agcgccacca agaggtgggg cttcaggagc ggcgtgcctc ccaaggtggt gagctacgag    300

gccggcgagt gggccgagaa ctgctacaac ctggagatca agaagcccga cggcagcgag    360

tgcctgcctc ctcctcctga cggcgtgagg ggcttcccca ggtgcaggta cgtgcacaag    420

gcccagggca ccggcccctg ccccggcgac tacgccttcc acaaggacgg cgccttcttc    480

ctgtacgaca ggctggccag caccgtgatc tacaggggcg tgaacttcgc cgagggcgtg    540

atcgccttcc tgatcctggc caagcccaag gagaccttcc tgcagagccc tcccatcagg    600

gaggccgtga actacaccga gaacaccagc agctactacg ccaccagcta tctagagtac    660

gagatcgaga acttcggcgc ccagcacagc accaccctgt tcaagatcga caacaacacc    720

ttcgtgaggc tggacaggcc ccacacccct cagttcctgt tccagctgaa cgacaccatc    780

cacctgcacc agcagctgag caacaccacc ggcaggctga tctggaccct ggacgccaac    840

atcaacgccg acatcggcga gtgggccttc tgggagaaca agaagaacct gagcgagcag    900

ctgaggggcg aggagctgag cttcgaggcc ctgagcctga acgagaccga ggacgacgac    960

gccgccagca gcaggatcac caagggcagg atcagcgaca gggccaccag gaagtacagc   1020

gacctggtgc ccaagaacag ccccggcatg gtgcccctgc acatccccga gggcgagacc   1080

accctgccca gccagaacag caccgagggc aggagggtgg gcgtgaacac ccaggagacc   1140

atcaccgaga ccgccgccac catcatcggc accaacggca accacatgca gatcagcacc   1200

atcggcatca ggcccagcag cagccagatc cccagcagca gccccaccac cgcccctagc   1260

cccgaggccc agacccccac cacccacacc agcggaccca gcgtgatggc caccgaggag   1320

cccaccaccc ctcccggcag cagccccgga cccaccaccg aggcccctac cctgaccacc   1380

cctgagaaca tcaccaccgc cgtgaagacc gtgctgcccc aggagagcac cagcaacggc   1440

ctgatcacca gcaccgtgac cggcatcctg ggcagcctgg gcctgaggaa gaggagcagg   1500

aggcagacca acaccaaggc caccggcaag tgcaacccca acctgcacta ctggaccgcc   1560

caggagcagc acaacgccgc cggcatcgcc tggattccct acttcggccc cggcgccgag   1620

ggcatctaca ccgagggcct gatgcacaac cagaacgccc tggtgtgcgg cctgaggcag   1680

ctggccaacg agaccaccca ggccctgcag ctgttcctga gggccaccac cgagctgagg   1740

acctacacca tcctgaacag gaaggccatc gacttcctgc tgaggaggtg gggcggcacc   1800

tgcaggattc tgggccccga ctgctgcatc gagccccacg actggaccaa gaacatcacc   1860

gacaagatca accagatcat ccacgacttc atcgacaacc ctctgcccaa ccaggacaac   1920

gacgacaact ggtggaccgg ctggcggcag tggatacctg ccggcatcgg catcaccggc   1980

atcatcatcg ccatcatcgc tctgctgtgc gtgtgcaagc tgctgtgctg a             2031
```

-continued

<210> SEQ ID NO 3
<211> LENGTH: 2028
<212> TYPE: DNA
<213> ORGANISM: Ebola virus
<220> FEATURE:
<223> OTHER INFORMATION: Ebola virus (EBOV) transmembrane envelope glycoprotein (GP) Sudan/Gulu type species (SEBOV) wild type filovirus antigen

<400> SEQUENCE: 3

```
atgggggtc ttagcctact ccaattgccc agggacaaat ttcggaaaag ctctttcttt     60

gtttgggtca tcatcttatt ccaaaaggcc ttttccatgc ctttgggtgt tgtgactaac    120

agcactttag aagtaacaga gattgaccag ctagtctgca aggatcatct tgcatctact    180

gaccagctga aatcagttgg tctcaacctc gaggggagcg gagtatctac tgatatccca    240

tctgcaacaa agcgttgggg cttcagatct ggtgttcctc ccaaggtggt cagctatgaa    300

gcgggagaat gggctgaaaa ttgctacaat cttgaaataa agaagccgga cgggagcgaa    360

tgcttacccc caccgccaga tggtgtcaga ggctttccaa ggtgccgcta tgttcacaaa    420

gcccaaggaa ccgggccctg cccaggtgac tacgcctttc acaaggatgg agctttcttc    480

ctctatgaca ggctggcttc aactgtaatt tacagaggag tcaattttgc tgagggggta    540

attgcattct tgatattggc taaaccaaaa gaaacgttcc ttcagtcacc ccccattcga    600

gaggcagtaa actacactga aaatacatca agttattatg ccacatccta cttggagtat    660

gaaatcgaaa attttggtgc tcaacactcc acgacccttt tcaaaattga caataatact    720

tttgttcgtc tggacaggcc ccacacgcct cagttccttt tccagctgaa tgataccatt    780

caccttcacc aacagttgag taatacaact gggagactaa tttggacact agatgctaat    840

atcaatgctg atattggtga atgggctttt tgggaaaata aaaaaaatct ctccgaacaa    900

ctacgtggag aagagctgtc tttcgaagct ttatcgctca acgagacaga agacgatgat    960

gcggcatcgt cgagaattac aaagggaaga atctccgacc gggccaccag gaagtattcg   1020

gacctggttc caaagaattc ccctgggatg gttccattgc acataccaga aggggaaaca   1080

acattgccgt ctcagaattc gacagaaggt cgaagagtag gtgtgaacac tcaggagacc   1140

attacagaga cagctgcaac aattataggc actaacggca accatatgca gatctccacc   1200

atcgggataa gaccgagctc cagccaaatc ccgagttcct caccgaccac ggcaccaagc   1260

cctgaggctc agacccccac aacccacaca tcaggtccat cagtgatggc caccgaggaa   1320

ccaacaacac caccgggaag ctcccccggc ccaacaacag aagcacccac tctcaccacc   1380

ccagaaaata taacaacagc ggttaaaact gtcctgccac aggagtccac aagcaacggt   1440

ctaataactt caacagtaac agggattctt gggagtcttg ggcttcgaaa acgcagcaga   1500

agacaaacta acaccaaagc cacgggtaag tgcaatccca acttacacta ctggactgca   1560

caagaacaac ataatgctgc tgggattgcc tggatcccgt actttggacc gggtgcggaa   1620

ggcatataca ctgaaggcct gatgcataac caaaatgcct tagtctgtgg acttaggcaa   1680

cttgcaaatg aaacaactca agctctgcag cttttcttaa gagccacaac ggagctgcgg   1740

acatatacca tactcaatag gaaggccata gatttccttc tgcgacgatg gggcgggaca   1800

tgcaggatcc tgggaccaga ttgttgcatt gagccacatg attggacaaa aaacatcact   1860

gataaaatca accaaatcat ccatgatttc atcgacaacc ccttacctaa tcaggataat   1920

gatgataatt ggtggacggg ctggagacag tggatccctg caggaatagg cattactgga   1980

attattattg caattattgc tcttctttgc gtttgcaagc tgctttgc                2028
```

-continued

<210> SEQ ID NO 4
<211> LENGTH: 2043
<212> TYPE: DNA
<213> ORGANISM: Artificial Sequence
<220> FEATURE:
<223> OTHER INFORMATION: synthetic Marburg virus (MARV) transmembrane envelope glycoprotein (GP) Angola type species codon optimized filovirus antigen

<400> SEQUENCE: 4
atgaagacca cctgcctgct gatcagcctg atcctgatcc agggcgtgaa gaccctgccc 60
atcctggaga tcgccagcaa catccagccc cagaacgtgg acagcgtgtg cagcggcacc 120
ctgcagaaga ccgaggacgt gcacctgatg ggcttcaccc tgagcggcca gaaggtggcc 180
gacagccctc tggaggccag caagaggtgg gccttcaggg ccggcgtgcc ccccaagaac 240
gtggagtaca ccgagggcga ggaggccaag acctgctaca acatcagcgt gaccgacccc 300
agcggcaaga gcctgctgct ggaccctccc accaacatca gggactaccc taagtgcaag 360
accatccacc acatccaggg ccagaaccct cacgcccagg gcatcgccct gcacctgtgg 420
ggcgccttct tcctgtacga caggatcgcc agcaccacca tgtacagagg aaaagtgttc 480
acagagggaa acatcgctgc tatgatcgtg aacaagaccg tgcataagat gatcttcagc 540
agacagggac agggatatag acatatgaac ctgacatcca caaacaagta ctggacaagc 600
agcaacggaa cacagacaaa cgatacagga tgttttggaa cactgcagga atacaactcc 660
accaagaacc agacatgtgc ccctagcaag aagcctctgc ctctgcctac agctcatcct 720
gaagtgaagc tgacatccac aagcacagat gccacaaagc tgaacacaac agatcctaat 780
agcgacgacg aggatctgac aacaagcgga tccggatccg gagaacagga accttataca 840
acaagcgacg ctgctacaaa acagggactg tcctccacaa tgcctcctac acctagccct 900
cagcctagca cacctcagca gggaggcaac aacacaaacc attcccaggg agtggtgaca 960
gaacctggaa agacaaacac aacagcccag cctagcatgc ctcctcataa cacaacaaca 1020
atcagcacaa acaacacctc caagcacaat ctgagcacac ctagcgtgcc tattcagaat 1080
gccaccaact acaacacaca gtccacagcc cctgaaaacg aacagacctc cgccccttcc 1140
aaaacaaccc tgctgcctac agaaaaccct acaacagcca agagcacaaa cagcacaaag 1200
agccctacaa caacagtgcc taacacaaca aacaagtata gcacaagccc tagccctaca 1260
cctaattcca cagctcagca tctggtgtat tttagaagaa agagaaacat cctgtggaga 1320
gaaggagata tgttcccttt tctggatgga ctgatcaacg ctcctatcga ttttgatcct 1380
gtgcctaaca caaagacaat ctttgatgaa agcagcagca gcggagcctc cgccgaagaa 1440
gatcagcatg cctcccctaa catcagcctg acactgagct attttcctaa ggtgaacgaa 1500
aacacagccc attccggaga aaacgaaaac gattgtgatg ccgaactgag aatctggagc 1560
gtgcaggaag atgatctggc cgccggactg agctggatcc cttttttttgg gcccggaatt 1620 gaaggactgt acaccgccgg cctgatcaag aaccagaaca acctggtgtg caggctgagg 1680
aggctggcca accagaccgc caagagcctg gagctgctgc tgagggtgac caccgaggag 1740
aggaccttca gcctgatcaa caggcacgcc atcgacttcc tgctggctag gtggggcggc 1800
acctgcaagg tgctgggccc cgactgctgc atcggcatcg aggacctgag caggaacatc 1860
agcgagcaga tcgaccagat caagaaggac gagcagaagg agggcaccgg ctggggcctg 1920
ggcggcaagt ggtggaccag cgactgggga gtgctgacaa acctgggaat cctgctgctg 1980

-continued

| | |
|---|---|
| ctgagcattg ccgtgctcat tgctctgtcc tgtatctgta gaatctttac caagtacatc | 2040 |
| gga | 2043 |

ADENOVIRUS SEROTYPE 26 AND SEROTYPE 35 FILOVIRUS VACCINES

CROSS-REFERENCE TO RELATED APPLICATIONS

This application is a national phase entry under 35 U.S.C. §371 of International Patent Application PCT/US2011/064944, filed Dec. 14, 2011, designating the United States of America and published in English as International Patent Publication WO2012/082918 A1 on Jun. 21, 2012, which claims the benefit under Article 8 of the Patent Cooperation Treaty to U.S. Provisional Patent Application Ser. No. 61/422,954, filed Dec. 14, 2010.

TECHNICAL FIELD

This disclosure relates to biotechnology and adenoviral vectors for inducing protective immunity against filovirus infection.

BACKGROUND

Replication-defective adenovirus vectors (rAd) are powerful inducers of cellular immune responses and have therefore come to serve as useful vectors for gene-based vaccines particularly for lentiviruses and filoviruses, as well as other nonviral pathogens (Shiver, et al., (2002) *Nature* 415(6869): 331-5; Hill, et al., *Hum Vaccine* 6(1): 78-83; Sullivan, et al., (2000) *Nature* 408(6812): 605-9; Sullivan et al., (2003) *Nature* 424(6949): 681-4; Sullivan, et al., (2006) PLoS Med 3(6): e177; Radosevic, et al., (2007); Santra, et al., (2009) *Vaccine* 27(42): 5837-45.) Adenovirus-based vaccines have several advantages as human vaccines since they can be produced to high titers under GMP conditions and have proven to be safe and immunogenic in humans (Asmuth, et al., *J Infect Dis* 201(1): 132-41; Kibuuka, et al., *J Infect Dis* 201(4): 600-7; Koup, et al., *PLoS One* 5(2): e9015; Catanzaro, et al., (2006) *J Infect Dis* 194(12): 1638-49; Harro, et al., (2009) *Clin Vaccine Immunol* 16(9): 1285-92.) While most of the initial vaccine work was conducted using rAd5 due to its significant potency in eliciting broad antibody and CD8+ T cell responses, pre-existing immunity to rAd5 in humans may limit efficacy (Catanzaro, (2006); Cheng, et al., (2007) *PLoS Pathog* 3(2): e25; McCoy, et al., (2007) *J Virol* 81(12): 6594-604; Buchbinder, et al., (2008) *Lancet* 372 (9653): 1881-93). This property might restrict the use of rAd5 in clinical applications for many vaccines that are currently in development including Ebolavirus (EBOV) and Marburg virus (MARV).

To circumvent the issue of pre-existing immunity to rAd5, several alternative vectors are currently under investigation. These include adenoviral vectors derived from rare human serotypes and vectors derived from other animals, such as chimpanzees (Vogels, et al., (2003) *J Virol* 77(15): 8263-71; Abbink, et al., (2007) *J Virol* 81: 4654-63; Santra, (2009)). Research on the use of animal-derived adenoviral vectors is relatively nascent, while human adenoviruses possess the advantages of having well-characterized biology and tropism on human cells, as well as documented manufacturability (Vogels, et al., (2007) *J Gen Virol* 88(Pt 11): 2915-24.). Immunogenicity of these vectors and their potential as vaccines has been demonstrated in animal models, primarily as prime-boost combinations with heterologous vectors (Abbink, et al., 2007; Shott et al., (2008) Vaccine 26:2818-23).

Adenovirus seroprevalence frequencies are cohort-dependent (Mast, et al., (2010) *Vaccine* 28(4): 950-7) but among a large group of 51 human adenoviruses tested, Ad35 and Ad11 were the most rarely neutralized by sera from 6 geographic locations (Vogels, et al., 2003). rAd35 vaccines have been shown to be immunogenic in mice, nonhuman primates, and humans, and are able to circumvent Ad5 immunity (Barouch, et al., (2004) *J Immunol* 172(10): 6290-7; Nanda, et al., (2005) *J Virol* 79(22): 14161-8; Ophorst, et al., (2006) *Infect Immun* 74(1): 313-20; Thorner, et al., (2006) *J Virol* 80(24): 12009-16; Rodriguez, et al., (2009) *Vaccine* 27(44): 6226-33). rAd35 vectors grow to high titers on cell lines suitable for production of clinical-grade vaccines (Havenga, et al., (2006) *J Gen Virol* 87(Pt 8): 2135-43), and have been formulated for injection as well as stable inhalable powder (Jin, et al., Vaccine 28(27): 4369-75). These vectors show efficient transduction of human dendritic cells (de Gruijl, et al., (2006) *J Immunol* 177(4): 2208-15; Lore, et al., (2007) *J Immunol* 179(3): 1721-9), and thus have the capability to mediate high level antigen delivery and presentation. Ad26, from subgroup D, is another adenovirus selected for its ability to circumvent Ad5 pre-existing immunity. Although Ad26 seroprevalence can be significant in certain in adult population, Ad26 neutralizing antibody titers remain markedly lower than Ad5 neutralizing antibody titers (Abbink, et al., 2007; Mast, et al., 2010). Studies have shown that rAd26 can be grown to high titers in Ad5 E1-complementing cell lines suitable for manufacturing these vectors at a large scale and at clinical grade (Abbink, et al., 2007), and this vector has been shown to induce humoral and cell-mediated immune responses in prime-boost vaccine strategies (Abbink, et al., 2007; Liu, et al., (2009) *Nature* 457(7225): 87-91).

BRIEF SUMMARY OF THE DISCLOSURE

The disclosure is based, at least in part, the discovery that rAd35 and rAd26 vectors upon single inoculation as well as heterologous prime-boost combinations generate protective immune responses against filovirus infection.

The disclosure thus provides isolated recombinant adenovirus vectors comprising nucleic acid encoding a filovirus antigen, wherein the adenovirus vector comprises an adenovirus 26 capsid protein (e.g., an rAd26 vector), or an adenovirus 35 capsid protein (e.g., an rAd35 vector). The adenovirus vector is typically replication defective.

The filovirus antigenic protein is usually a glycoprotein from an Ebola virus or a Marburg virus. The Ebola virus may be of any species, for example, *Zaire* or *Sudan/Gulu*. Exemplary nucleic acids encoding suitable filovirus antigens are shown in SEQ ID NO:1 and SEQ ID NO:2.

Also provided are isolated nucleic acid molecules encoding the recombinant adenovirus vectors hereof. The nucleic acids typically comprise an expression cassette comprising a CMV promoter operably linked to a polynucleotide sequence encoding the filovirus antigenic protein. The polynucleotide sequence encoding the filovirus antigenic protein may be SEQ ID NO:1 or SEQ ID NO:2.

Further provided are immunogenic compositions comprising the isolated adenovirus vectors hereof. The immunogenic composition may further comprise an adjuvant.

Also provided are methods of inducing an immune response against a filovirus antigen in a patient. The methods comprise administering to the patient an immunologically effective amount of the adenovirus vector hereof. Usually, the adenovirus vector is administered intramuscularly.

In some embodiments, the vectors are administered as a priming vaccination followed by a boosting vaccination. For example, the prime may be an administration of an adenovirus vector comprising an adenovirus 26 capsid protein and the boost may be an administration of an adenovirus vector comprising an adenovirus 35 capsid protein.

DEFINITIONS

An "adenovirus capsid protein" refers to a protein on the capsid of an adenovirus (e.g., Ad 26 or Ad 35) that is involved in determining the serotype and/or tropism of a particular adenovirus. Adenoviral capsid proteins typically include the fiber, penton and/or hexon proteins. As used herein an "Ad26 capsid protein" or an "Ad35 capsid protein" may be, for example, a chimeric capsid protein that includes at least a part of an Ad26 or Ad35 capsid protein. In certain embodiments, the capsid protein is an entire capsid protein of Ad26 or of Ad35. In certain embodiments, the hexon, penton and fiber are of Ad26 or of Ad35.

The terms "adjuvant" and "immune stimulant" are used interchangeably herein, and are defined as one or more substances that cause stimulation of the immune system. In this context, an adjuvant is used to enhance an immune response to the adenovirus vectors hereof.

The term "corresponding to," when applied to positions of amino acid residues in sequences, means corresponding positions in a plurality of sequences when the sequences are optimally aligned.

The terms "identical" or percent "identity," in the context of two or more nucleic acids or polypeptide sequences, (e.g., adenovirus capsid proteins hereof and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

An "isolated" nucleic acid molecule or adenovirus vector is a nucleic acid molecule (e.g., DNA or RNA) or virus, which has been removed from its native environment. For example, recombinant DNA molecules contained in a vector are considered isolated for the purposes of the disclosure. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the disclosure. Isolated nucleic acid molecules according to the disclosure further include such molecules produced synthetically.

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs."

A "polypeptide" is a polymer of amino acid residues joined by peptide bonds, whether produced naturally or synthetically. Polypeptides of less than about 50 amino acid residues are commonly referred to as "oligopeptides."

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents, such as carbohydrate groups are generally not specified, but may be present nonetheless.

The phrase "substantially identical," in the context of two nucleic acids or polypeptides hereof (e.g., adenovirus capsid proteins or filovirus antigens), refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al., (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides hereof are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "substantially similar" in the context of the capsid proteins or filovirus antigens hereof indicates that a polypeptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

DETAILED DESCRIPTION

Figure 1:
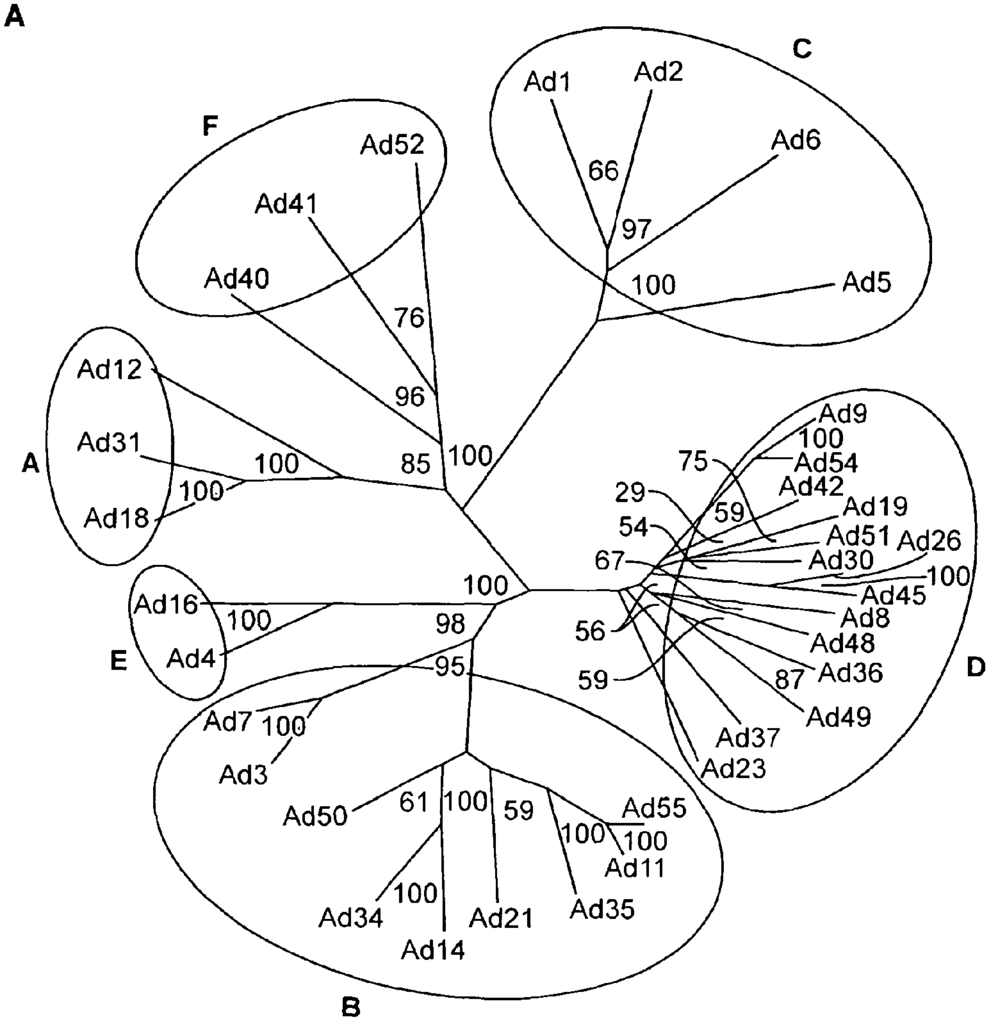
FIG. 1. Adenovirus genetic grouping and vector organization. (A) Phylogenetic tree showing the relationship of the adenovirus hexon sequences. The different subgroups A until F are indicated and human adenovirus serotypes 26 and 35 are highlighted. The tree was constructed using the neighbor-joining method of the ClustalX package (Larkin et al., 2007) and drawn using the Phylip Phylogeny Inference package version 3.68. Confidence values are displayed at internal branches as a percent of 1000 times bootstrap. (B) Schematic overview of the genome of recombinant Ad26 and recombinant Ad35 vectors. Both vectors have a full deletion of E1 and contain an expression cassette containing the EBOV glycoprotein gene under control of the CMV promoter. Further deletions were made in the E3 regions and the respective E4 orf6 sequences were replaced by the Ad5 E4orf6 sequences to facilitate the replication of these vaccine vectors on Ad5 E1 complementing cell lines like PER.C6® cells.
Figure 1:
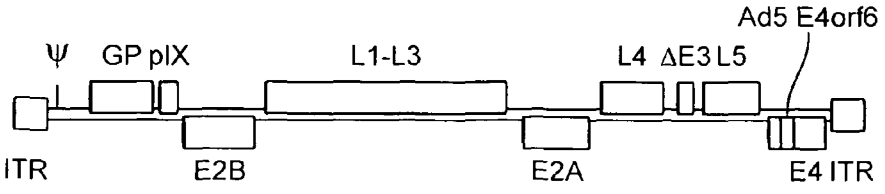

The disclosure is based upon, at least in part, the finding that rAd35 and rAd26 vectors upon single inoculation as well as heterologous prime-boost combinations generate protective immune responses against filovirus infection. In particular, the disclosure provides evidence that heterologous prime-boost combinations (in particular, Ad26 prime followed by Ad35 boost) are surprisingly effective in generating protective immune responses. The surprising effectiveness of these prime-boost combinations could not have been predicted at the time hereof. Thus, the disclosure provides recombinant adenoviral vectors (rAd35 or rAd26) that express filovirus antigens. The adenoviral vectors can be formulated as vaccines and used to induce protective immunity against filovirus infections either alone or in prime-boost combinations.

Filovirus Antigens

The Ebola viruses, and the genetically-related Marburg virus, are filoviruses associated with outbreaks of highly lethal hemorrhagic fever in humans and primates in North America, Europe, and Africa (Peters, C. J. et al., in: Fields Virology, eds. Fields, B. N. et al., 1161-1176, Philadelphia, Lippincott-Raven, 1996; Peters, C. J. et al., 1994 Semin Virol 5:147-154). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein (sGP) and a 130 kDa transmembrane glycoprotein (GP) generated by RNA editing that mediates viral entry (Peters, C. J. et al., in: Fields Virology, eds. Fields, B. N. et al., 1161-1176, Philadelphia, Lippincott-Raven, 1996; Sanchez, A. et al., 1996 PNAS USA 93:3602-3607). Other structural gene products include the nucleoprotein (NP), matrix proteins VP24 and VP40, presumed nonstructural proteins VP30 and VP35, and the viral polymerase (reviewed in Peters, C. J. et al., in: Fields Virology, eds. Fields, B. N. et al., 1161-1176, Philadelphia, Lippincott-Raven, 1996).

The nucleic acid molecules may encode structural gene products of any filovirus species. There are five species of Ebola viruses, Zaire (type species, also referred to herein as ZEBOV), Sudan (also referred to herein as SEBOV), Reston, Bundibugyo, and Ivory Coast. There is a single species of Marburg virus (also referred to herein as MARV).

The particular antigen expressed in the vectors hereof is not a critical aspect of the disclosure. The adenoviral vectors hereof can be used to express proteins comprising an antigenic determinant of a wide variety of filovirus antigens. In a typical and preferred embodiment, the vectors hereof include nucleic acid encoding the transmembrane form of the viral glycoprotein (GP). In other embodiments, the vectors hereof may encode the secreted form of the viral glycoprotein (SGP), or the viral nucleoprotein (NP).

One of skill will recognize that the nucleic acid molecules encoding the filovirus antigenic protein may be modified, e.g., the nucleic acid molecules set forth herein may be mutated, as long as the modified expressed protein elicits an immune response against a pathogen or disease. Thus, as used herein, the term "filovirus antigenic protein" refers to a protein that comprises at least one antigenic determinant of a filovirus protein described above. The term encompasses filovirus antigens (i.e., gene products of a filovirus), as well as recombinant proteins that comprise one or more filovirus antigenic determinants.

In some embodiments, the protein may be mutated so that it is less toxic to cells (see e.g., WO/2006/037038). The disclosure also includes vaccines comprising a combination of nucleic acid molecules. For example, and without limitation, nucleic acid molecules encoding GP, SGP and NP of the *Zaire, Sudan* and Ivory Coast Ebola strains may be combined in any combination, in one vaccine composition.

Adenoviral Vectors

As noted above, exposure to certain adenoviruses has resulted in immune responses against certain adenoviral serotypes, which can affect efficacy of adenoviral vaccines. The disclosure provides adenoviral vectors comprising capsid proteins from two rare serotypes: Ad26 and Ad35. In the typical embodiment, the vector is an rAd26 or rAd35 virus.

Thus, the vectors hereof comprise an Ad26 or Ad35 capsid protein (e.g., a fiber, penton or hexon protein). One of skill will recognize that it is not necessary that an entire Ad26 or Ad35 capsid protein be used in the vectors hereof. Thus, chimeric capsid proteins that include at least a part of an Ad26 or Ad35 capsid protein can be used in the vectors hereof. The vectors hereof may also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of skill will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus hereof could combine the absence of pre-existing immunity of the Ad26 and Ad35 serotypes with characteristics, such as temperature stability, assembly, anchoring, production yield, redirected or improved infection, stability of the DNA in the target cell, and the like.

In certain embodiments the recombinant adenovirus vector hereof is derived mainly or entirely from Ad35 or from Ad26 (i.e., the vector is rAd35 or rAd26). In some embodiments, the adenovirus is replication deficient, e.g., because it contains a deletion in the E1 region of the genome. For the adenoviruses hereof, being derived from Ad26 or Ad35, it is typical to exchange the E4-orf6 coding sequence of the adenovirus with the E4-orf6 of an adenovirus of human subgroup C, such as Ad5. This allows propagation of such adenoviruses in well known complementing cell lines that express the E1 genes of Ad5, such as, for example, 293 cells, PER.C6 cells, and the like (see, e.g., Havenga et al., 2006, *J Gen Virol* 87: 2135-43; WO 03/104467). In certain embodiments, the adenovirus is a human adenovirus of serotype 35, with a deletion in the E1 region into which the nucleic acid encoding the antigen has been cloned, and with an E4 orf6 region of Ad5. In certain embodiments, the adenovirus is a human adenovirus of serotype 26, with a deletion in the E1 region into which the nucleic acid encoding the antigen has been cloned, and with an E4 orf6 region of Ad5. For the Ad35 adenovirus, it is typical to retain the 3' end of the E1B 55K open reading frame in the adenovirus, for instance the 166 bp directly upstream of the pIX open reading frame or a fragment comprising this, such as a 243 bp fragment directly upstream of the pIX start codon, marked at the 5' end by a Bsu36I restriction site, since this increases the stability of the adenovirus because the promoter of the pIX gene is partly residing in this area (see, e.g., Havenga et al., 2006, supra; WO 2004/001032).

The preparation of recombinant adenoviral vectors is well known in the art. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811 and in Vogels et al., (2003) *J Virol* 77(15): 8263-71. An exemplary genome sequence of Ad35 is found in GenBank Accession AC_000019.

replication-defective by deletion or inactivation of regions critical to replication of the virus, such as the E1 region. The regions can be substantially deleted or inactivated by, for example, inserting the gene of interest (usually linked to a promoter). In some embodiments, the vectors hereof may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors hereof. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of filovirus antigenic proteins can be expressed in the vectors hereof. If required, the heterologous gene encoding the filovirus antigenic protein can be codon-optimized to ensure proper expression in the treated host (e.g., human). Codon-optimization is a technology widely applied in the art. Typically, the heterologous gene is cloned into the E1 and/or the E3 region of the adenoviral genome.

The heterologous filovirus gene may be under the control of (i.e., operably linked to) an adenovirus-derived promoter (e.g., the Major Late Promoter) or may be under the control of a heterologous promoter. Examples of suitable heterologous promoters include the CMV promoter and the RSV promoter. Preferably, the promoter is located upstream of the heterologous gene of interest within an expression cassette.

As noted above, the adenovirus vectors hereof can comprise a wide variety of filovirus antigens known to those of skill in the art. Table 1 provides a summary of exemplary vectors hereof.

TABLE 1

| Vector name | VRC number of source plasmid for insert | Sequence of insert | Description |
|---|---|---|---|
| Ad5.Ebo.GP(Z)FL.wt | 6001 | SEQ ID NO: 1 | ZEBOV GP wild type |
| Ad5.Ebo.GP(S/G)FL.wt | 6610 | SEQ ID NO: 3 | SEBOV GP wild type |
| Ad5.Mar.GP(A)FL | 6712 | SEQ ID NO: 4 | MARV Angola codon optimized |
| Ad26.Ebo.GP(Z)FL.wt | 6001 | SEQ ID NO: 1 | ZEBOV GP wild type |
| Ad26.Ebo.GP(S/G)FL.wt | 6610 | SEQ ID NO: 3 | SEBOV GP wild type |
| Ad26.Mar.GP(A)FL | 6712 | SEQ ID NO: 4 | MARV Angola codon optimized |
| Ad35BSU.Ebo.GP(Z)FL.wt | 6001 | SEQ ID NO: 1 | ZEBOV GP wild type |
| Ad35BSU.Ebo.GP(S/G)FL | 6611 | SEQ ID NO: 2 | SEBOV GP codon optimized |
| Ad35BSU.Mar.GP(A)FL | 6712 | SEQ ID NO: 4 | MARV Angola codon optimized |

Typically, a vector hereof is produced using a nucleic acid comprising the entire recombinant adenoviral genome (e.g., a plasmid, cosmid, or baculovirus vector). Thus, the invention also provides isolated nucleic acid molecules that encode the adenoviral vectors hereof. The nucleic acid molecules hereof may be in the form of RNA or in the form of DNA obtained by cloning or produced synthetically. The DNA may be double-stranded or single-stranded.

The adenovirus vectors hereof are typically replication defective. In these embodiments, the virus is rendered Immunogenic Compositions Purified or partially purified adenovirus vectors hereof may be formulated as a vaccine (also referred to as an "immunogenic composition") according to methods well known in the art. Such compositions may include adjuvants to enhance immune responses. The optimal ratios of each component in the formulation may be determined by techniques well known to those skilled in the art.

The preparation and use of immunogenic compositions are well known to those of skill in the art. Liquid pharmaceutical compositions generally include a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

The compositions are suitable for single administrations or a series of administrations. When given as a series, inoculations subsequent to the initial (priming) administration are given to boost the immune response and are typically referred to as booster inoculations. The compositions hereof can be used as a boosting composition primed by antigen using any of a variety of different priming compositions, or as the priming composition. Thus, one aspect of the disclosure provides a method of priming and/or boosting an immune response to an antigen in an individual. For example, in some preferred embodiments, a priming administration of one adenoviral vector hereof (e.g., rAd26) is followed by a booster inoculation of the second adenoviral vector (e.g., rAd35).

The timing of the administration of boosting compositions is well within the skill in the art. Boosting composition are generally administered weeks or months after administration of the priming composition, for example, about 2-3 weeks or 4 weeks, or 8 weeks, or 16 weeks, or 20 weeks, or 24 weeks, or 28 weeks, or 32 weeks or one to two years.

The compositions hereof may comprise other filovirus antigens or the priming or boosting inoculations may comprise other antigens. The other antigens used in combination with the adenovirus vectors hereof are not critical to the invention and may be, for example, filovirus antigens, nucleic acids expressing them, virus like particles (VLPs), or prior art viral vectors. Such viral vectors include, for example, other adenoviral vectors, vaccinia virus vectors, avipox vectors, such as fowlpox or canarypox, herpes virus vectors, a vesicular stomatitis virus vectors, or alphavirus vectors. One of skill will recognize that the immunogenic compositions hereof may comprise multiple antigens and vectors.

The antigens in the respective priming and boosting compositions (however many boosting compositions are employed) need not be identical, but should share antigenic determinants.

As noted above, the immunogenic compositions hereof may comprise adjuvants. Adjuvants suitable for co-administration in accordance with the disclosure should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be administered include lectins, growth factors, cytokines and lymphokines, such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids therefore.

As noted above, the compositions hereof may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Administration is typically intramuscular.

Intramuscular administration of the immunogenic compositions may be achieved by using a needle to inject a suspension of the adenovirus vector. An alternative is the use of a needless injection device to administer the composition (using, e.g., BIOJECTOR™) or a freeze-dried powder containing the vaccine.

For intravenous, cutaneous or subcutaneous injection, or injection at the site of affliction, the adenovirus vector will be in the foam of a parenterally acceptable aqueous solution which is pyrogen-free and has suitable pH, isotonicity and stability. Those of skill in the art are well able to prepare suitable solutions using, for example, isotonic vehicles, such as Sodium Chloride Injection, Ringer's Injection, and Lactated Ringer's Injection. Preservatives, stabilizers, buffers, antioxidants and/or other additives may be included, as required. A slow-release formulation may also be employed.

Typically, administration will have a prophylactic aim to generate an immune response against a filovirus antigen before infection or development of symptoms. Diseases and disorders that may be treated or prevented in accordance with the disclosure include those in which an immune response may play a protective or therapeutic role. In other embodiments, the adenovirus vectors can be administered for post-exposure prophylactics.

The immunogenic compositions containing the adenovirus vectors are administered to a subject, giving rise to an anti-filovirus immune response in the subject. An amount of a composition sufficient to in induce a detectable immune response is defined to be an "immunologically effective dose." As shown below, the immunogenic compositions hereof induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the adenovirus vectors may be administered to an individual, particularly human or other primate. Administration may be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but may be for use in an experimental context, for instance in investigation of mechanisms of immune responses to the adenovirus vector.

In one exemplary regimen, the adenovirus vector is administered (e.g., intramuscularly) in the range of from about 100 μl to about 10 ml of saline solution containing concentrations of from about $10^4$ to $10^{12}$ virus particles/ml. Typically, the adenovirus vector is administered in an amount of about $10^9$ to about $10^{12}$ viral particles (vp) to a human subject during one administration, more typically from about $10^{10}$ to about $10^{12}$ vp. An initial vaccination can be followed by a boost as described above. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The compositions hereof may be administered alone or in combination with other treatments, either simultaneously or sequentially dependent upon the condition to be treated.

EXAMPLES

The following examples are offered to illustrate, but not to limit the claimed invention.

There are distinct advantages associated with either single-shot or prime-boost immunization depending on the need for immediate versus long-term immunity must be taken into account when optimizing immunization regimens. EBOV and other filovirus outbreaks tend to occur suddenly and spread quickly among populations in which medical facilities are scarce. Thus, under these circumstances, short vaccine regimens may be desirable. For this reason, single-shot vaccinations with rAd5 vectors containing EBOV glycoprotein (GP) and nucleoprotein (NP) genes have been developed in non-human primates (Sullivan, et al., 2006). Such vaccines have been shown to elicit strong immune responses within one month (Sullivan, et al., 2003), probably due to high expression levels of the inserts and the tropism of Ad5 for dendritic cells. On the other hand, long-term protective immunity will likely require a prime-boost vaccine regimen comprising two or more administrations that can induce durable T-cell memory. Therefore, we designed a series of experiments to test immunogenicity and potency for both single inoculation and a prime-boost combinations using rAd35 and rAd26 vectors, and the results of these studies are presented herein.

Materials and Methods

Generation rAd Ebola vaccines. Low seroprevalent E1/E3-deleted rAd26 and rAd35 vaccine vectors expressing EBOV GPs were constructed, grown and purified as described previously (Abbink, et al., 2007). An Ad5 vector, not expressing EBOV GP, was constructed, grown and purified by the same method and used to induce immunity to Ad5 in selected animals as indicated in each experiment. EBOV GP inserts spanning the open reading frames of *Zaire* (SEQ ID NO:1) and *Sudan/Gulu* (SEQ ID NO:2) species were cloned under transcriptional control of the human CMV promoter and the SV-40 polyadenylation sequence into a plasmid containing the left portion of the Ad genome, including left ITR and packaging signal. Co-transfection of this plasmid with a cosmid containing the remaining Ad sequence (E3-deleted) to PER.C6® cells yielded an E1/E3-deleted replication deficient recombinant Ad26 or Ad35 vaccine vector. To facilitate replication of rAd26 and rAd35 vectors on PER.C6® cells, the native E4 orf6 regions were replaced by the Ad5 E4orf6 sequence (Havenga, et al., 2006). The rAd viruses were plaque purified and one plaque of each was expanded up to a production scale of approximately 2.4 L. A two step cesium chloride gradient ultracentrifugation procedure was used to purify the rAd EBOV vectors. The purified rAd EBOV vaccines were stored as single use aliquots below −65° C. Virus particle titers were determined measuring the optical density at 260 nm (Maizel, et al., 1968 *Virology* 36(1): 115-25). Infectivity was assessed by TCID50 using 911 cells (Fallaux, et al., (1996) *Hum Gene Ther* 7(2): 215-22). Adenovirus-mediated EBOV GP expression was assessed by infection of A549 cells followed by analysis of culture lysates on Western blot. The identity of the purified vectors was confirmed by PCR and the complete transgene regions, including flanking sequences were checked using DNA sequencing.

Phylogenetic Analysis. The phylogenetic tree was constructed using full length adenovirus hexon amino acid sequences. Amino acid sequences were aligned using the Clustal X programme (Larkin, et al., (2007) *Bioinformatics* 23(21): 2947-8) and the tree was built using the Clustal X Neighbour-Joining method and the tree was bootstrapped 1000 times. The tree was visualized and plotted using the Drawtree programme from the Phylip Phylogeny Inference package version 3.68.

Animal Challenge Study and Safety. Animal experiments were conducted in full compliance with all relevant federal guidelines and NIH policies. Cynomolgus macaques (*Macaca fascicularis*) 3-5 years of age and weighing between 2-3 kg were obtained from Covance for all studies. Monkeys were housed individually and given enrichment regularly as recommended by the Guide for the Care and Use of Laboratory Animals (DHEW number NIH 86-23). Animals were anesthetized with ketamine prior to blood sampling or vaccination. Each vaccine group in this study contained three cynomolgus macaques, and each control group contained a single cynomolgus macaque. Four weeks post EBOV vaccination, animals were transferred to the Maximum Containment Laboratory (BSL-4) for infection with a target dose of 1,000 PFU of *Zaire* EBOV delivered by the intramuscular route into the caudal thigh. The ZEBOV challenge stock was prepared from a human fatality in the 1995 outbreak in the former *Zaire*. Animals remained there until the completion of the study. While in the BSL-4 facility the monkeys were fed and checked at a minimum of once daily.

Animal studies performed in BSL-4 biocontainment at USAMRIID were approved by the USAMRIID Institutional Animal Care and Use Committee. Animal research was conducted in compliance with the Animal Welfare Act and other Federal statutes and regulations relating to animals and experiments involving animals and adheres to the principles stated in the *Guide for the Care and Use of Laboratory Animals*, National Research Council, 1996. The facilities used are fully accredited by the Association for Assessment and Accreditation of Laboratory Animal Care International.

Animal Immunization. Subjects received intramuscular vaccinations in the bi-lateral deltoids by needle and syringe with doses and vectors indicated in each experiment. Selected animals, as indicated in each experiment, were pre-immunized with $10^{11}$ PFU of an empty Ad5 vector to induce Ad5 immunity. Ad5 ELISA antibody titers were established in these animals prior to EBOV vaccination.

Anti-EBOV GP IgG ELISA. Polyvinyl chloride ELISA plates (Dynatech, Vienna, Va., or Nunc, Rochester, N.Y.) were coated with 100 μl of antigen per well and incubated at 4° C. overnight. Subsequent incubations were performed at room temperature. Transmembrane-deleted EBOV GP (EBOV GPΔTM) generated by calcium phosphate-mediated transient transfection of 293T cells served as the antigen. Plates were washed six times with PBS containing Tween 20 after antigen coating. Test sera were serially diluted to 7 concentrations ranging from 1:50 to 1:50,000 and added to the antigen-coated wells for 60 minutes. The plates were washed six times followed by incubation with detection antibody, goat anti-human IgG (H+L; Chemicon/Millipore, Billerica, Mass.) conjugated to horseradish peroxide. Sigma Fast o-Phenylenediamine Dihydrochloride (Sigma, St. Louis, Mo.) substrate was added to the wells and the optical density was determined (450 nm). A prevaccination serum sample for each animal was run every time the assay was performed. A positive control serum sample from a single animal with a known *Zaire* EBOV GP IgG response was run every time the assay was performed. Background-subtracted ELISA titers are expressed as EC90, reciprocal optical density values, which represent the dilution at which there is a 90% decrease in antigen binding.

Intracellular Cytokine Staining. Whole blood samples from cynomolgus macaques were subjected to density gradient centrifugation over Ficoll to isolate peripheral blood mononuclear cells (PBMC). Approximately $1\times10^6$ cells were stimulated in 100 μl RPMI medium containing 10% heat inactivated fetal calf serum for 6 hours at 37° C. with anti-CD28 (clone CD28.2) and -CD49d (clone L25) antibodies (BD Biosciences), Brefeldin-A (Sigma-Aldrich, St. Louis, Mo.), and either DMSO or a pool of peptides spanning the entire *Zaire* EBOV GP open reading frame. The peptides were 15-mers overlapping by 11 amino acids reconstituted in fresh sterile DMSO at a final concentration of 2.5 μg/ml for each peptide. For each sample equivalent an aliquot was stimulated with SEB as a positive control. After the six hour stimulation, PBMC were stained with a mixture of antibodies against lineage markers (CD3-Cy7-APC, clone SP34-2 (BD Biosciences), CD4-QD605 clone M-T477 (BD Biosciences), CD8-TRPE clone RPA-T8, CD95 Cy5-PE, clone DX2 (BD Biosciences), CD45RA QD655, clone 5H3, at room temperature for 20 min. The CD45RA QD655 and CD8-TRPE antibodies were conjugated according to standardized protocols as previously described (Koup et al., 2010 Priming Immunization with DNA Augments Immunogenicity of Recombinant Adenoviral Vectors for Both HIV-1 Specific Antibody and T-Cell Responses. PLoS One 5(2): e9015. doi:10.1371/journal.pone.0009015). After 2 washes the cells were fixed and permeabilized with Cytofix/Cytoperm (BD Biosciences) followed by staining with antibodies against cytokines TNFα-APC, clone MAb11 (BD Biosciences), and IL-2 PE, clone MQ17H12 (BD Biosciences). The viability dye ViViD (Invitrogen) was included to allow discrimination between live and dead cells (Perfetto, et al., (2006) *J Immunol Methods* 313(1-2): 199-208). Samples were acquired on an LSR II cytometer (BD Biosciences), collecting up to 1,000,000 events and analyzed using FlowJo 9.1 and SPICE 5.0 software (Tree Star). Cytokine positive cells were defined as a percentage within $CD4^+$ and $CD8^+$ T cell memory subsets. Memory subsets were defined as CD45RA±/CD95+ or CD28±/CD95+. In the later case, CD28 Alexa488 (clone 28.2, BioLegend) was used for stimulation instead of unconjugated CD28 mAb.

Serum Biochemistry. For challenge studies, blood was collected from the NHP on days 0, 3, 6, 10, 14 and 28 post *Zaire* EBOV infection. Total white blood cell counts, white blood cell differentials, red blood cell counts, platelet counts, hematocrit values, total hemoglobin, mean cell volume, mean corpuscular volume, and mean corpuscular hemoglobin concentration were determined from blood samples collected in tubes containing EDTA, by using a laser-based hematologic Analyzer (Coulter Electronics, Hialeah, Fla., USA). Serum samples were tested for concentrations of aspartate aminotransferase (AST), by using a Piccolo Point-Of-Care Blood Analyzer (Abaxis, Sunnyvale, Calif., USA).

Detection of EBOV. Virus titration was performed by plaque assay on Vero cells. Briefly, increasing 10-fold dilutions of plasma samples were adsorbed to Vero monolayers in duplicate wells (0.2 ml per well); thus, the limit for detection was 25 pfu/ml.

Statistics. Comparison of anti-GP ELISA IgG titers, and intracellular cytokine production by T cells memory subsets was done using a two-tailed T test in GraphPad Prism software.

Results

Figure 2:
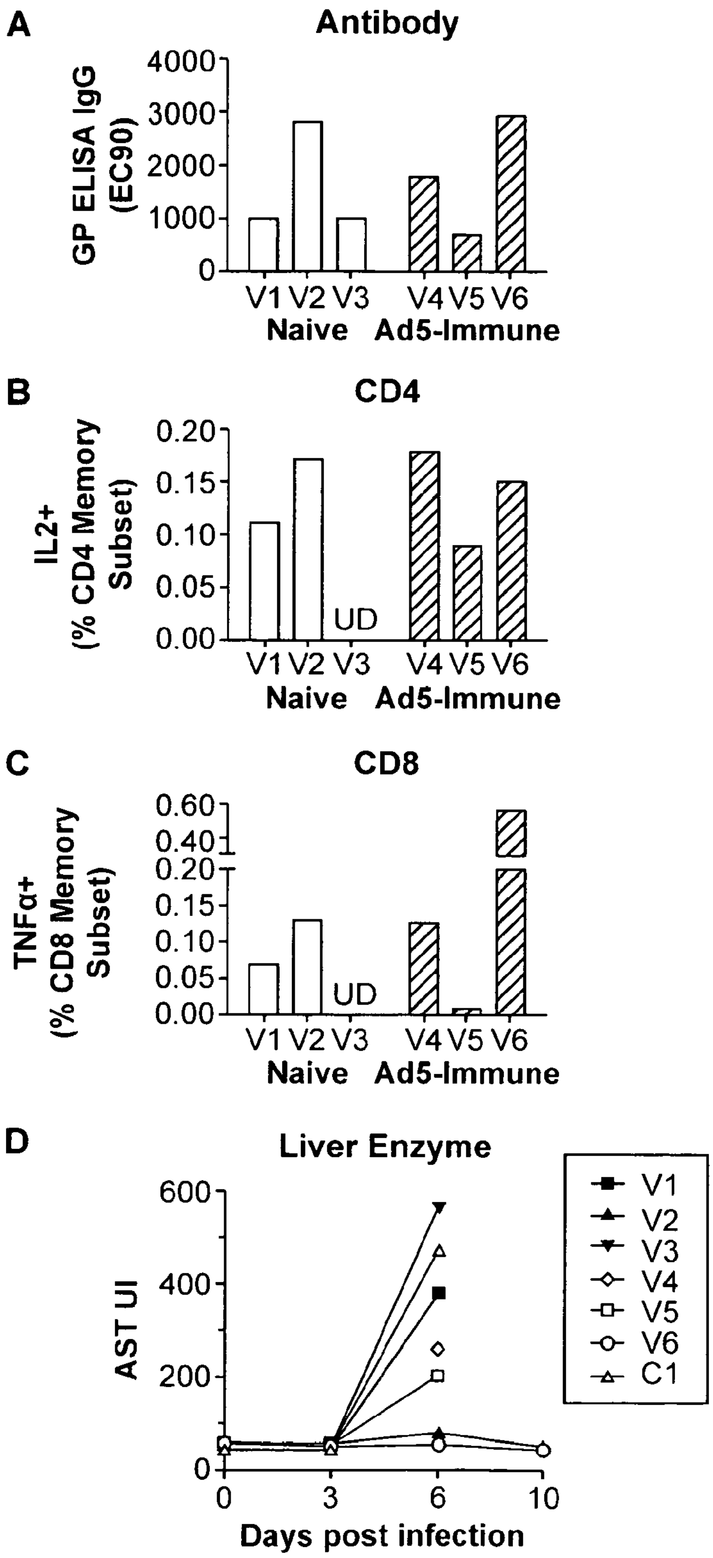
FIG. 2. rAd35-GP (using Ad35BSU.Ebo.GP(Z)FL.wt) vaccine-induced immune responses and EBOV challenge. (A) The quantity of anti-EBOV GP IgG in plasma samples obtained 3 weeks after vaccination from Ad5-naïve (gray bars) and Ad5-immune (black bars), rAd35-GP vaccinated cynomolgus macaques determined by ELISA. EC90 antibody titers were determined as described in Methods. (B, C) Frequency of antigen-specific $CD4^+$ and $CD8^+$ T-lymphocyte responses enumerated in the memory cell subsets by ICS for IL-2 (CD4) or TNF-α (CD8), and analysis by flow cytometry after stimulation of week 3 post-vaccine PBMC. (D) Plasma AST liver enzyme levels in rAd35-GP vaccinated (blue, Ad5-naïve; red, Ad5-immune) and control (black) macaques after infectious challenge with 1000 PFU ZEBOV.

Adenovirus Phylogeny and Vector Construction. rAd5 genetic vaccines for EBOV provide potent protective immunity in macaques, and have been proven safe and immunogenic in human clinical trials (Asmuth, et al.; Kibuuka, et al.; Harro, et al., 2009;). Studies in macaques and humans have shown that-pre-existing vector directed immunity can limit the potency of viral vector-based vaccines (McCoy, et al., 2007; Buchbinder, et al., 2008). Since seroprevalence data suggest that a large proportion of humans worldwide have experienced natural infection with Ad5we evaluated other adenovirus serotypes for use as vaccine vectors (FIG. 1A). Ad35, a group B and Ad26, a group D adenovirus segregate genetically from rAd5, Group C, so we hypothesized that vaccine vectors derived from these serotypes will be less sensitive to Ad5 immunity in primates. Although Ad35 and Ad26 vectors use receptors distinct from Ad5 usage, they nonetheless demonstrate efficient transduction of monocyte-derived dendritic cells, and circumvent Ad5 immunity in mice. Therefore, GP inserts from the *Zaire* or *Sudan/Gulu* species of EBOV were cloned under transcriptional control of the human CMV promoter into the E1 region of rAd35 and rAd26 vectors (FIG. 1B). Both vector genomes have been deleted in the E1 genes in order to render them replication deficient and reduce the potential for recombination in vaccinated subjects.

rAd35 vaccination and induction of immune responses in macaques. Initial studies were conducted with a single EBOV species-vaccine encoding the GP from *Zaire*Ebolavirus (ZEBOV), GP(Z), to test the ability of rAd35 vectors to induce immune responses in Ad5 naïve macaques, and also to evaluate vector potency within the context of pre-existing immunity to Ad5. Six cynomolgus macaques, three Ad5-naïve and three Ad5-immune, were each vaccinated intramuscularly with $10^{10}$ particles of rAd35-GP(Z) (Ad35BSU.Ebo.GP(Z)FL.wt) by needle injection. At three weeks post-vaccination, antigen-specific antibody and T-cell responses were evaluated in peripheral blood samples obtained from individual subjects. Antibodies against EBOV-GP(Z) assessed by ELISA were induced in all subjects, demonstrating that rAd35-GP(Z) vectors mediated successful in vivo transduction of target cells and efficient antigen presentation (FIG. 2A). Ad5-naïve and Ad5-immune subjects generated serum antibody titers ranging from approximately 1:700 to 1:3000. These antibody levels are in the range that has been observed for Ad5-based vaccines containing GP(Z) inserts and exceed the minimum value (1:500) that has been associated with immune protection against EBOV infection in this macaque-Ad vaccine model (Sullivan, 2009). Although significant antibody titers were induced in all vaccinees, none of the subjects exceeded the threshold titer (ca. 1:3500) that predicts 100% protection following administration of Ad5-GP vaccine vectors in macaques. It is noteworthy, however, that comparison of antibody titers in Ad5-naïve versus Ad5-immune subjects showed that there was no significant difference in average titers elicited among these groups (1:1600 vs 1:1800 respectively), suggesting that rAd35 vectors are effective vaccines in subjects who have been exposed previously to Ad5.

Cellular immune responses were evaluated by intracellular cytokine staining (ICS) for either TNF-α ($CD8^+$) or IL-2 ($CD4^+$) after stimulation of subject PBMC with overlapping peptides spanning the EBOV GP(Z) open reading frame.

Surface staining of lymphocytes using CD45RA and CD95 was performed to assess antigen-specific immune responses in the memory subpopulations of $CD4^+$ and $CD8^+$ T-cells (FIGS. 2B and 2C). As observed for antibody responses, macaques vaccinated with the rAd35 vector generated cellular immunity against EBOV-GP, and the frequency of antigen-specific T-cells was not affected by Ad5 immune status. The rank order magnitude of cellular responses in both $CD4^+$ and $CD8^+$ lymphocytes across subjects was similar to antibody responses, although the frequency of antigen-specific T-cells for one subject V3 was below detectable levels. Previous studies in macaques have shown that rAd5-based vaccine vectors induce $CD8^+$ T cell frequencies that are dominant over $CD4^+$ responses. In the present study, rAd35-vaccinated subjects generated GP-specific $CD4^+$ and $CD8^+$ lymphocyte at similar frequencies. However, given the relatively small number of subjects tested, it is possible that differences, if present, could not be revealed. Altogether these results demonstrate that rAd35-GP is immunogenic in cynomolgus macaques and that vector potency for the induction of antigen-specific humoral and cell-mediated immune responses is not reduced in subjects with pre-existing immunity to Ad5.

Challenge of rAd35-Vaccinated Macaques with ZEBOV. We next tested whether vaccination with rAd35-GP provides protection against infectious challenge with a high dose of ZEBOV. One week after the assessment of immune responses shown above, the six rAd35-GP vaccinated and one naïve cynomolgus macaque were exposed to 1000 PFU of the 1995 Kikwit strain of ZEBOV by intramuscular injection. Hepatic enzymes were measured regularly after infectious challenge since elevations in these markers are characteristic of productive EBOV infection in macaques. Circulating levels of aspartate transaminase (AST) were evaluated every 3-4 days during the acute infection period, through day 10-14 (FIG. 2D), and then on the last day of the 28-day follow up period (not shown). Plasma AST remained at baseline levels through day 3 after infection in all subjects, indicating normal liver function immediately following infectious EBOV challenge. By day 6 after EBOV exposure, the unvaccinated control subject displayed a 10-fold increase in enzyme levels indicating active infection in this subject. Blood samples from two subjects in the Ad5-naïve/rAd35-vaccinated group (V1, V3) also exhibited dramatic increases in AST, while the third subject in this group V2 showed only a marginal increase at a single time point prior to resolution back to baseline levels. Similarly, two of three subjects in the Ad5-immune/rAd35-vaccinated group (V4, V5) displayed elevations in AST, though much lower than the unvaccinated control, while one subject V6 remained normal for this parameter of infection. Overall, AST levels were higher in Ad5-naive than in the Ad5-immune vaccinated subjects. It is noteworthy mentioning that each subject who remained normal for this clinical observation displayed the highest prechallenge, antigen-specific $CD8^+$ and antibody responses within its respective vaccine group. Plasma viremia levels (FIG. 2E) confirmed EBOV infection in all animals who displayed elevated AST.

The results of this experiment show that rAd35 is immunogenic when administered at a dose of $10^{10}$ particles per subject. The vaccine generated protective immune responses but this dose and regimen was suboptimal for uniform protection of all subjects. Within vaccine groups, protective immunity was associated with the highest magnitude antigen-specific antibody and $CD8^+$ T-cell responses.

rAd35-GP dose response effects on induction of protective immunity. rAd-based vectors are commonly administered to macaques in doses ranging from $10^{10}$ to $10^{12}$ particles. Previous results with rAd5-GP have demonstrated $10^{10}$ virus particles as the minimal dose to achieve 100% protection of cynomolgus macaques against EBOV infection (Sullivan, 2006). Since the studies described above were performed at the lower end of this dose range and did not result in uniform protection, it is possible that even marginally lower in vivo antigen expression achieved with the rAd35 vector when compared to that of rAd5 vectors could result in suboptimal immune responses. Therefore, we asked whether administration of a higher vaccine dose could elicit a greater degree of immune protection. The vaccine in this experiment also included rAd35 expressing GP from the Sudan EBOV species (S/G) in order to compare efficacy to historical data with rAd5 vaccines that comprised GP from both *Sudan* and *Zaire* species. In the present study, cynomolgus macaques (n=3 per group) were vaccinated with $10^{10}$ or $10^{11}$ virus particles each of Ad35BSU.Ebo.GP(Z)FL.wt and Ad35BSU.Ebo.GP(S/G)FL and immune responses were measured three weeks after vaccination in the previous experiment.

Figure 3:
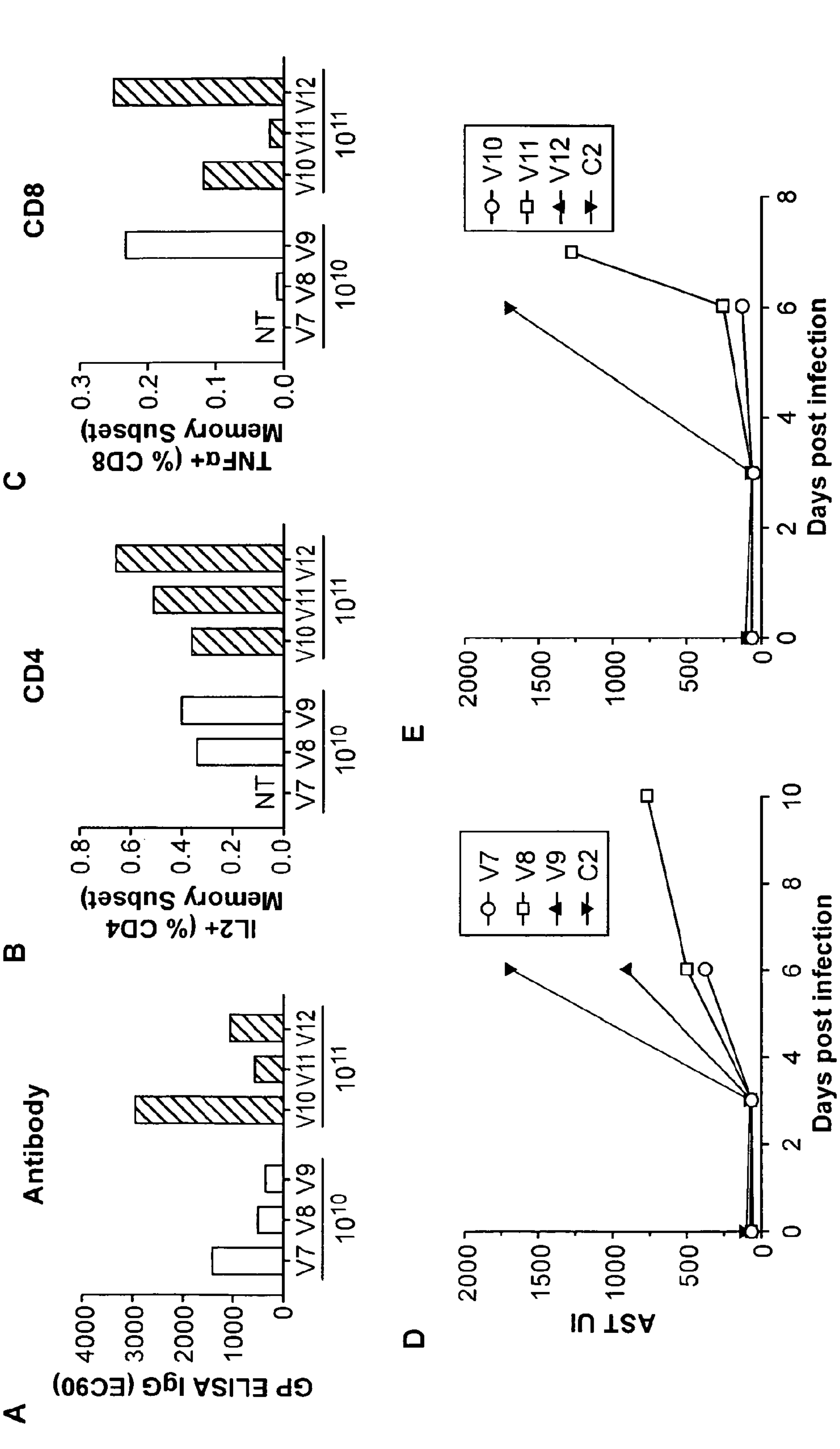
FIG. 3. Dose response for rAd35-GP induction of immune responses in macaques (using Ad35BSU.Ebo.GP(Z)FL.wt and Ad35BSU.Ebo.GP(S/G)FL). (A) GP-specific ELISA IgG antibody titers (EC90) in plasma obtained from macaques 3 weeks after vaccination with $10^{10}$ or $10^{11}$ virus particles of each of the rAd35-GP vectors (Ad35BSU.Ebo.GP(Z)FL.wt and Ad35BSU.Ebo.GP(S/G) FL). (B, C) Antigen-specific $CD4^+$ and $CD8^+$ T cell frequencies assessed by ICS as in FIG. 2. Gray bars, $10^{10}$ virus particles rAd35-GP; black bars, $10^{11}$ virus particles rAd35-GP. (D, E) Plasma AST liver enzyme levels following challenge with 1000 PFU ZEBOV. Blue, $10^{10}$ virus particles of rAd35-GP; red, $10^{11}$ virus particles rAd35-GP and black, control.

GP-specific antibodies were generated in all subjects (FIG. 3A), an expected result since the vaccine dose was equal to or higher than that in the previous experiment. However, the titers in two subjects vaccinated with $10^{10}$ particles in this experiment (V8, V9) were 1:340 and 1:500, respectively, levels near or below the minimum cutoff previously observed to predict protection in Ad5-GP vaccinated subjects (Sullivan, et al., 2009). The maximum antibody titer observed was 1:2,900 (subject V10) which is the same as the maximum titers observed in the rAd35 subjects shown in FIG. 2. Average antibody titers were higher in the $10^{11}$ dose group (1:1500 vs 1:700) but the difference did not reach statistical significance (p=0.02). As observed in the lower dose group, there was one subject whose titer was near the rAd5-GP vaccine cutoff for immune protection (subject V11, 1:540).

$CD4^+$ and $CD8^+$ T-cell responses were present in both dose groups at three weeks post vaccination. There was no clear dose response in either $CD4^+$ or $CD8^+$ T cell responses. Since the kinetics of cellular immune responses varies between subjects, especially in outbred animals, and the response measurement is not cumulative over time as it is with antibody levels, group trends are sometimes difficult to capture at a single time point. Within each individual, antigen-specific T-cell frequencies were higher for $CD4^+$ than for $CD8^+$ cells, but when combined with the results from the first experiment, there was no trend toward either $CD4^+$ or $CD8^+$ cell dominance induced by rAd35-GP vectors in these experiments.

One week following the assessment of immune responses, all six vaccinated macaques and one unvaccinated subject were exposed to 1000 PFU ZEBOV by intramuscular injection and observed for signs of productive infection. Hemorrhagic manifestations of EBOV infection routinely result in the appearance of a maculopapular rash on the face and extremities of infected macaques; subjects also typically reduce food intake and become dehydrated. The earliest appearance of symptoms for the two unvaccinated subjects occurred on day 6 after EBOV exposure; each displayed a full constellation of symptoms by day 7 (data not shown). Table 2 shows the infectious challenge outcomes and the day of death in nonsurvivors for both rAd35 studies. The unvaccinated subjects succumbed to the lethal effects of infection on days 9 and 8 (Experiment 1 and 2, respectively). Vaccinated subjects who died were similar to control, unvaccinated subjects, except that they survived on average two days longer than controls, suggesting a potential partial immune benefit of vaccination even though mortality was ultimately observed. The number of survivors was greater in the subjects who received rAd35-GP(Z) only, compared to those receiving GP(Z) plus GP(S/G) irrespective of the vaccine dose, but differences in survival rates were not significant across any vaccine groups in the two challenge experiments.

TABLE 2

| Experiment | Subject ID | Vaccine Group | Symptoms | Outcome |
|---|---|---|---|---|
| 1 | V1 | Naive/ Ad35BSU.Ebo.GP(Z)FL.wt at $10^{10}$ | Rash d6, anorexia d6, dehydration d6 | Died day 7 |
| | V2 | Naive/ Ad35BSU.Ebo.GP(Z)FL.wt at $10^{10}$ | Anorexia d6 | Survived |
| | V3 | Naive/ Ad35BSU.Ebo.GP(Z)FL.wt at $10^{10}$ | Rash d6, anorexia d6, dehydration d6 | Died day 8 |
| | V4 | Immune/ Ad35BSU.Ebo.GP(Z)FL.wt at $10^{10}$ | Rash d7, anorexia d6, dehydration d7 | Died day 8 |
| | V5 | Immune/ Ad35BSU.Ebo.GP(Z)FL.wt at $10^{10}$ | Rash d6, anorexia d6, dehydration d7 | Died day 9 |
| | V6 | Immune/ Ad35BSU.Ebo.GP(Z)FL.wt at $10^{10}$ | Anorexia d6 | Survived |
| 2 | V7 | Ad35BSU.Ebo.GP(Z)FL.wt and Ad35BSU.Ebo.GP(S/G)FL, each at $10^{10}$ | Rash d6, anorexia d6, dehydration d6 | Died day 6 |
| | V8 | Ad35BSU.Ebo.GP(Z)FL.wt and Ad35BSU.Ebo.GP(S/G)FL, each at $10^{10}$ | Rash d6, anorexia d6, dehydration d9 | Died day 10 |
| | V9 | Ad35BSU.Ebo.GP(Z)FL.wt and Ad35BSU.Ebo.GP(S/G)FL, each at $10^{10}$ | Rash d6, anorexia d6, dehydration d6 | Died day 6 |
| | V10 | Ad35BSU.Ebo.GP(Z)FL.wt and Ad35BSU.Ebo.GP(S/G)FL, each at $10^{11}$ | Rash d6, anorexia d6, dehydration d7 | Died day 7 |
| | V11 | Ad35BSU.Ebo.GP(Z)FL.wt and Ad35BSU.Ebo.GP(S/G)FL, each at $10^{11}$ | Rash d6, anorexia d6, dehydration d7 | Died day 7 |
| | V12 | Ad35BSU.Ebo.GP(Z)FL.wt and Ad35BSU.Ebo.GP(S/G)FL, each at $10^{11}$ | Rash d6, anorexia d6, dehydration d6 | Died day 8 |
| 1 | C1 | None | Rash d6, anorexia d6, dehydration d6 | Died day 9 |
| 2 | C2 | None | Rash d7, anorexia d6, dehydration d6 | Died day 8 |

Figure 4:
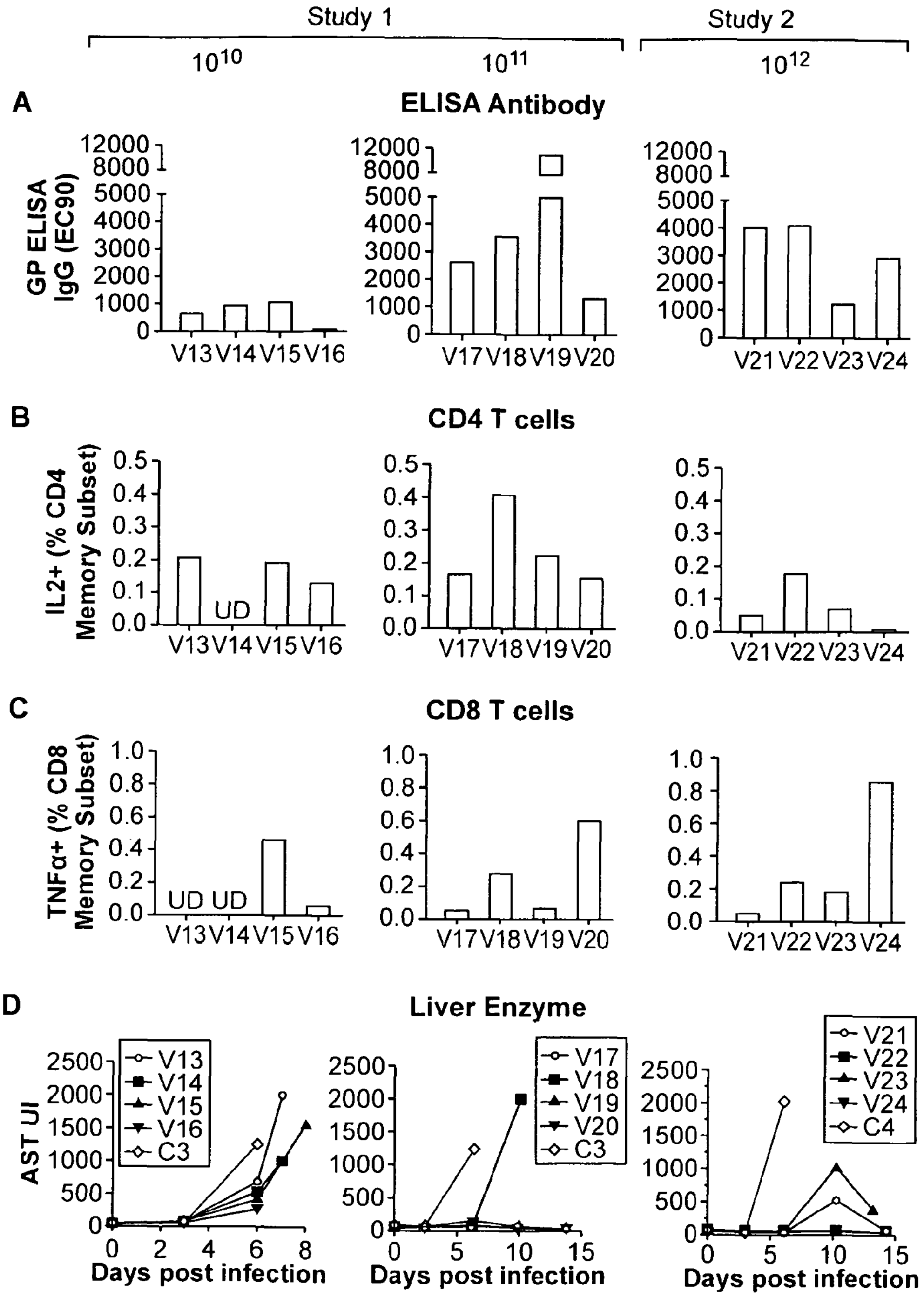
FIG. 4. Ability of rAd26-GP vectors to induce antigen-specific antibody and T-lymphocyte responses in cynomolgus macaques (using Ad26.Ebo.GP(Z)FL.wt and Ad26.Ebo.GP(S/G)FL.wt). (A) ELISA IgG antibody titers (EC90), and (B, C) frequencies of GP-specific $CD4^+$ and $CD8^+$ T cells, (D) Plasma AST liver enzymes are shown for individual cynomolgus macaques in two separate studies. Study 1 subjects received a vaccine dose of either $10^{10}$ or $10^{11}$ rAd26 virus particles of each of the rAd26-GP vectors (Ad26.Ebo.GP(Z)FL.wt and Ad26.Ebo.GP(S/G)FL.wt) and Study 2 subjects received a dose of $10^{12}$ virus particles of each of the rAd26-GP vectors (Ad26.Ebo.GP(Z)FL.wt and Ad26.Ebo.GP(S/G)FL.wt).

Altogether, the studies using rAd35 as a vaccine vector with GP(Z) alone or in combination with GP(S/G) showed that antigen delivery and presentation was sufficient to generate antigen-specific immune responses, but at levels below what is required for absolute immune protection. Lower protective immunity was associated with the antibody levels detected in some animals consistent with what has been shown using rAd5 vectors to be marginal for protection.

rAd26-GP vaccine immunogenicity and potency for protection against EBOV infection. We next evaluated a recombinant Ad26-based vaccine, a group D adenovirus, for its ability to generate protective immunity against EBOV infection. This serotype uses the same cellular receptor (CD46) as Ad35 but has been shown to generate slightly higher immune responses when used as a priming vaccine vector (Liu, et al., 2009). For these studies, dose escalation was conducted over a range of three orders of magnitude in two separate infectious challenge experiments. In the first study we tested the vaccine at doses of $10^{10}$ or $10^{11}$ particles for each vector, Ad26.Ebo.GP(Z)FL.wt and Ad26.Ebo.GP(S/G) FL.wt, and in the second study we used a dose of $10^{12}$ particles each. The first study tested the vaccine in Ad5-immune cynomolgus macaques in order to evaluate whether rAd26, like rAd35, could elicit antigen-specific immune response in the presence of pre-existing immunity to Ad5. Four Ad5-immune cynomolgus macaques per group were vaccinated by intramuscular injection, and blood samples were obtained three weeks later to assess circulating humoral and cellular immune responses against EBOV GP (FIG. 4A). The average circulating anti-GP antibody titers showed a dose response across dose groups; 1:700 for $10^{10}$ vaccinees and 1:4500 for subjects receiving $10^{11}$ particles ($p=0.06$). The average titer for three of four subjects in the $10^{10}$ dose group was just above the minimum threshold for immune protection in rAd5-vaccinated subjects (1:500), but subject V16 generated only a marginal antibody response, 1:100, which was well below the predicted protection cutoff for an Ad5-GP vaccine. In contrast, subject V19 who was vaccinated with $10^{11}$ particles of the rAd26 vaccine generated a very high antibody titer, 1:10,500, exceeding by nearly three-fold the level that has been associated with complete immune protection (1:3,500), while the others in this vaccine group displayed intermediate titers that do not definitively predict survival outcome. In study two, four subjects received $10^{12}$ particles of each rAd26 vector and generated antibody responses very similar to those in the $10^{11}$ dose group, with the majority of subject's titers between 1:1000-1:4000. The average anti-GP antibody titer for this group was 1:3000.

T-cell immune responses (FIGS. 4B and 4C) were measured by ICS as in the rAd35 studies and also trended toward a dose response in study one, but the difference between $10^{10}$ and $10^{11}$ dose groups was not significant (p=0.12 and 0.26 for $CD4^+$ and $CD8^+$, respectively). Average antigen-specific $CD4^+$ T-cell frequencies were 0.14% for vaccinees receiving $10^{10}$ particles rAd26-GP versus 0.24% at the higher vaccine dose, and one vaccinee in the lower dose group, subject V14, had an undetectable $CD4^+$ response (FIG. 4B). The rAd26 vaccine did not skew cellular immune responses toward either $CD4^+$ or $CD8^+$ dominance; the $CD8^+$ frequencies, 0.13% and 0.25% ($10^{10}$ and $10^{11}$ vaccine doses, respectively) essentially mirrored the magnitude of $CD4^+$ responses. In the case of $CD8^+$ T cells, there were two subjects in the low dose group, V13 and V14, with undetectable antigen-specific responses (FIGS. 4B and 4C). In rAd26 study two, average antigen-specific $CD8^+$ frequencies (0.34%) were higher than $CD4^+$ responses (0.08%) but this apparent skewing toward $CD8^+$ responses was driven primarily by a single subject, V24, who had very high $CD8^+$ frequencies and low $CD4^+$ responses. Otherwise, overall cellular immune responses were similar to those observed in rAd26 study one.

Figure 5:
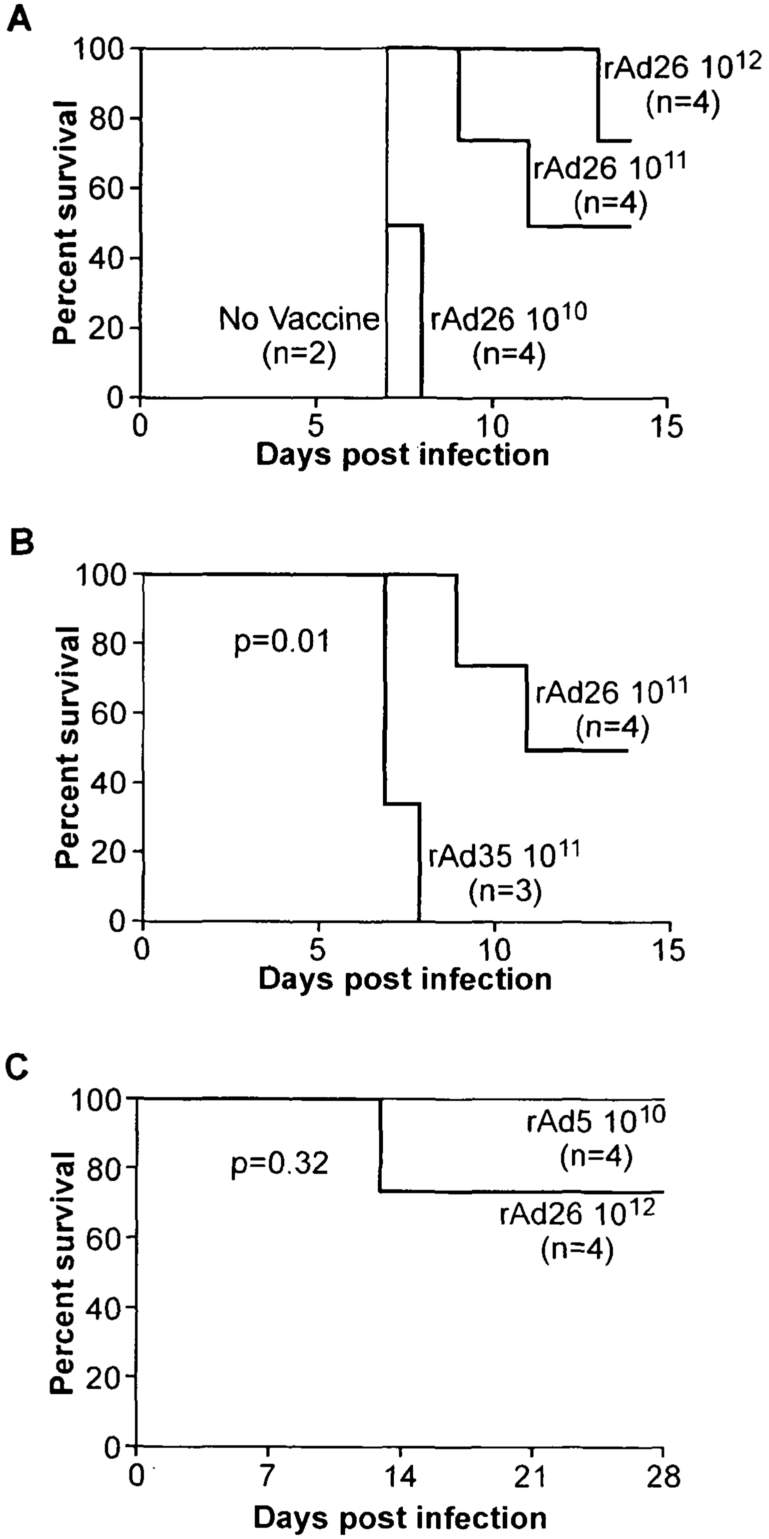
FIG. 5. Kaplan-Meier survival curves for rAd26-GP vaccinated macaques (using Ad26.Ebo.GP(Z)FL.wt and Ad26.Ebo.GP(S/G)FL.wt). Unvaccinated control and animals vaccinated with rAd26-GP were infected four weeks after vaccination with 1000 PFU ZEBOV in two separate challenge experiments as shown in FIG. 4. Panel A: Black lines show unvaccinated subjects and dark blue lines show Ad26-vaccinated subjects at doses indicated. Panel B: one group of rAd35-vaccinated subjects (light blue) is shown for potency comparison with Ad26 at a dose of $10^{11}$ virus particles of each the rAd26-GP vectors (Ad26.Ebo.GP(Z)FL.wt and Ad26.Ebo.GP(S/G)FL.wt). Panel C: Historical Ad5-vaccinated macaque survival (red) compared to subjects vaccinated with $10^{12}$ virus particles of each the rAd26-GP vectors (Ad26.Ebo.GP(Z)FL.wt and Ad26.Ebo.GP(S/G)FL.wt).

Infectious EBOV challenges were performed by IM injection of 1000 PFU ZEBOV at 4 weeks after vaccination for each of the rAd26 vaccine studies, and liver enzyme levels were measured to monitor disease (FIG. 4D). Unvaccinated subjects exhibited manifestations of hepatic injury between days 3 and 6 of infection. All subjects receiving the lowest dose rAd26 vaccine, $10^{10}$ particles, showed similar signs disease, though AST levels increased at a slower rate. As predicted from this clinical indicator, all subjects in this group succumbed to the lethal effects of infection by day 8 post ZEBOV challenge (FIG. 5A). The antibody and T-cell responses were low or undetectable in some subjects in this group. Differences in the magnitude of immune responses between the dose groups in Ad26 study one ($10^{10}$ and $10^{11}$) were generally reflected in the survival rates, with a higher survival outcome, 2 out of 4 protected, in subjects vaccinated with $10^{11}$ particles of rAd26-GP (p=0.01). Ad26 at $10^{11}$ particles was superior not only to the lower dose, but also provided greater protection than rAd35-GP when matched for dosage (FIG. 5B). Finally, rAd26 given at a dose of $10^{12}$ particles yielded the highest number of survivors (3 out of 4) for any vaccine regimen tested in these studies, and the level of immune protection did not differ significantly from what has been observed previously with rAd5 vectors (p=0.32, FIG. 5C); however, this survival rate was obtained using a higher dose for rAd26 than for rAd5, $10^{12}$ vs. $10^{10}$ particles, respectively, suggesting a potential potency difference between these vectors in this animal model.

Figure 6:
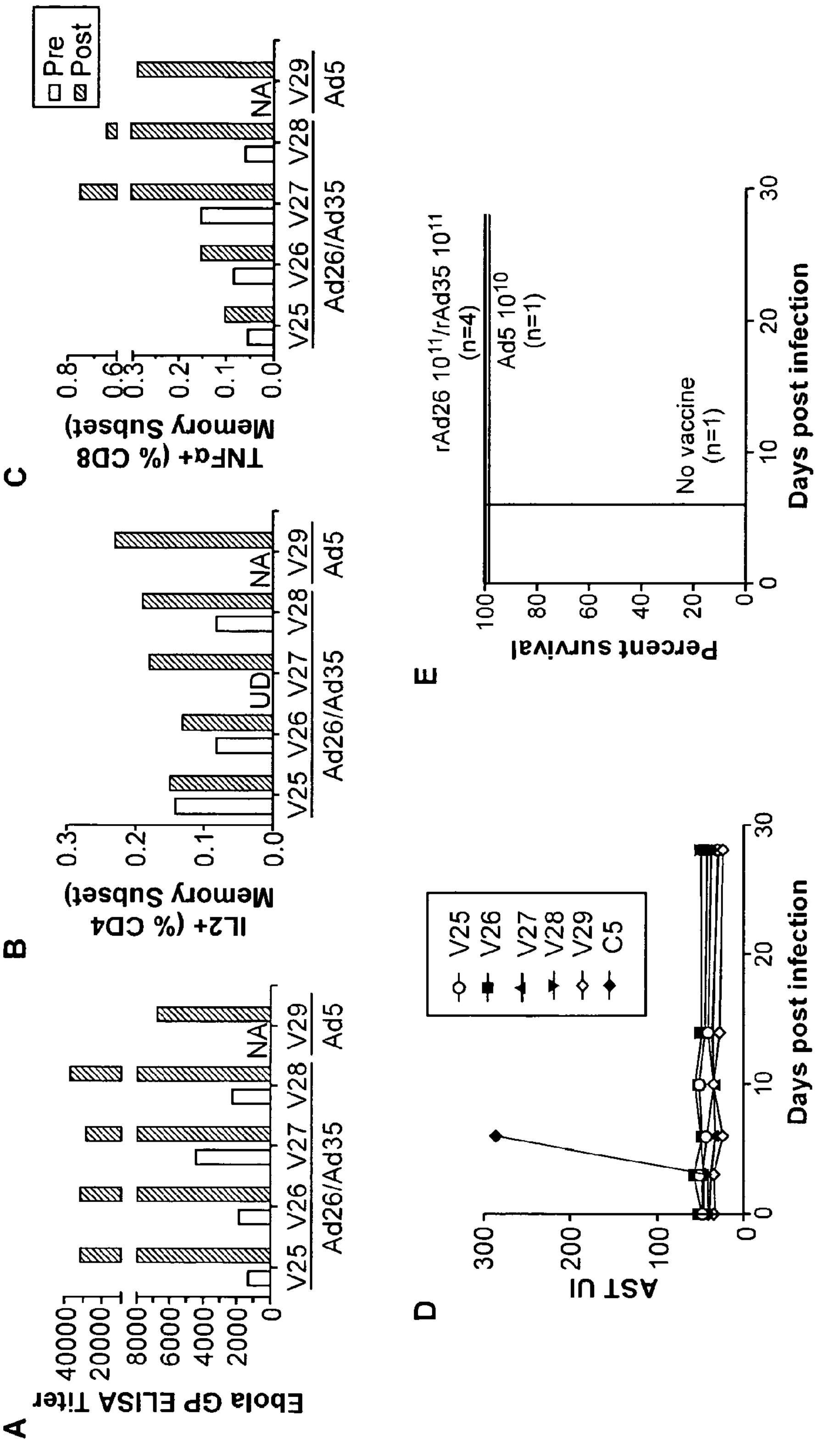
FIG. 6. Comparison of prime and boost immune responses after rAd26-GP/rAd35-GP vaccinations (using Ad26.Ebo.GP(Z)FL.wt and Ad26.Ebo.GP(S/G)FL.wt followed by Ad35BSU.Ebo.GP(Z)FL.wt and Ad35BSU.Ebo.GP(S/G)FL). (A) The quantity of anti-EBOV GP IgG in plasma samples obtained 3 weeks after vaccination from Ad5-naïve (gray bars) and Ad5-immune (black bars), rAd35-GP vaccinated cynomolgus macaques determined by ELISA. EC90 antibody titers were determined as described in Methods. (B, C) Frequency of antigen-specific $CD4^+$ and $CD8^+$ T-lymphocyte responses enumerated in the memory cell subsets by ICS for IL-2 (CD4) or TNF-α (CD8), and analysis by flow cytometry after stimulation of week 3 post-vaccine PBMC. (D, E) EBOV challenge results. Plasma AST liver enzyme levels (D), and Kaplan-Meier survival curve (E) for rAd26-GP/rAd35-GP vaccinated macaques after infectious challenge with 1000 PFU ZEBOV (blue, rAd26-GP/rAd35-GP; red, Ad5-GP and black, unvaccinated control).

Heterologous Prime-Boost with rAd26 and rAd35 Vectors. The dose-response characteristics for rAd26-GP-mediated immune protection and the high survival outcome using $10^{12}$ vector particles suggested that this vector efficiently induces GP-antigen expression. Since it has been shown for EBOV and other pathogens, in both nonhuman and human subjects, that heterologous prime-boost vaccination can elicit more potent immunity than single shot immunization (Sullivan Nature 2000; Sampra et al., Vaccine 27 (2009) 5837-5845; Koup, et al, PLoS One 2010; Geisbert et al., (2010) *Virol* 84(19): 10386-94), we asked whether rAd26-GP immune responses could be boosted with a heterologous vector to improve protection against EBOV infection. Four cynomolgus macaques were inoculated with $10^{11}$ particles each of Ad26.Ebo.GP(Z)FL.wt and Ad26.Ebo.GP(S/G) FL.wt. One month later, all subjects received a boost vaccination with the same dose of Ad35BSU.Ebo.GP(Z)FL.wt and Ad35BSU.Ebo.GP(S/G)FL. Immune responses were assessed immediately prior to, and three weeks following the boost. FIG. 6A shows that antibody responses against EBOV-GP(Z) were efficiently induced by the priming vaccination. Individual subjects generated EC90 antibody titers against GP from 1:2700 to 1:7100, and the average titer for the group was 1:4000, consistent with the responses observed in the previous study testing $10^{11}$ rAd26 as a single inoculation vaccine (1:4500). This study included for comparison a single subject inoculated with $10^{10}$ particles each of rAd5-GP(Z) and rAd5-GP(S/G), whose post vaccination antibody titer was 1:6800. Subsequent inoculation of the rAd26-GP-primed subjects with $10^{11}$ particles of rAd35-GP vectors boosted antigen-specific antibody levels approximately one order of magnitude for most vaccinees to an average titer of 1:32,000, except subject V27 whose post-prime antibody titers were exceptionally high. Interestingly, the boost vaccination generated more uniform titers across subjects, with a standard deviation across subjects of just under 10%, compared to the post prime titers that exhibited a standard deviation of 54%.

Cellular immune responses were also boosted markedly by rAd35-GP administration to rAd26-vaccinated macaques (FIGS. 6B and 6C). $CD4^+$ T cells were boosted in all except in one subject, V25; the average increase after rAd35-GP administration was 2-fold across all subjects and boosting revealed a measurable response in subject V27 whose response was undetectable prior to boosting. Final, post-boost $CD4^+$ T-cell frequencies were comparable to those generated by rAd5-GP vaccination. The boost effect was greatest for $CD8^+$ T cells and all subjects exhibited the boost effect in this cellular compartment yielding, in two subjects (V27 and V28), responses exceeding those generated by rAd5-GP vaccination. Average GP-specific CD8+ T-cell frequencies measured by ICS were 0.09% after primary immunization, and increased 4.7-fold to 0.41%, 3 weeks after secondary vaccination with rAd35-GP.

Altogether, the immunogenicity results above showed that rAd35-GP vectors are potent for boosting rAd26-GP primed macaques. Post-boost GP-directed antibodies were induced to an average level that is nearly a log higher than the level predictive for 100% immune protection in rAd5-GP vaccinated primates (Sullivan, et al., 2009). Importantly, rAd35-GP boost provided a substantial enhancement of $CD8^+$ T-cell frequencies, also shown to associate with immune protection against EBOV infection. Therefore, one week after assessment of immune responses (4-weeks post boost) all vaccinated subjects and one unvaccinated control macaque were exposed to 1000 PFU of ZEBOV by intramuscular injection. The control subject exhibited clinical symptoms characteristic of EBOV infection and succumbed to lethal effects at day 6 after challenge (FIGS. 6C and 6D). In contrast, all vaccinated subjects remained normal for circulating AST levels (FIG. 6C), and exhibited no evidence of hemorrhagic disease in gross pathology evaluation at study termination (not shown). All four vaccinated subjects survived infectious challenge and remained symptom-free throughout the 28-day follow up period until study termination. These results showed that rAd26/rAd35 vectors administered as a heterologous prime boost vaccine regimen provides uniform immune protection against ZEBOV infection, and demonstrate the potential utility of this approach for achieving additive or synergistic results with combination vaccines.

Discussion

Adenoviruses perform well as vaccine vectors for the delivery of a variety of viral bacterial and parasitic antigens (Lasaro et al., (2009) *Mol Ther* 17(8): 1333-9). rAd5 vectors in particular generate potent antigen-specific immune responses in mice, nonhuman primates, and humans, as we have observed when EBOV-GP is the target antigen. However, preclinical and human clinical studies have suggested that the potency of rAd5-based vectors may be compromised in individuals who have been exposed previously to Ad5 if they have high level of immunity against the vector. The aim of the studies herein was to identify rAd vectors that can deliver the EBOV GP antigen in both naïve and Ad5-immune subjects. Since pre-existing immunity against any viral vector has the potential to limit its effectiveness, we focused our attention on viruses that infect humans relatively rarely, as indicated by the prevalence of seropositive subjects and/or the low levels of neutralizing antibodies. The rare human adenovirus serotypes, Ad35 and Ad26 were selected for vaccine development in the current work.

rAd35-GP vaccination of macaques generated antigen-specific antibody and T-cell responses in individual subjects within the range observed previously when rAd5 was used as the delivery vector. The average anti-GP antibody titer for all rAd35 vaccinees (irrespective of dose), 1:1400 was lower than the average for all historical subjects vaccinated with $10^{10}$ rAd5-GP (1:11,000, n=17), providing an initial indication that vector potency might differ between the two serotypes if antibody titer is the same correlate for rAd35 as it is for rAd5 EBOV vaccines. $CD4^+$ and $CD8^+$ T-cell responses were detectable in most subjects prior to infectious challenge, though the absolute magnitude cannot be compared to rAd5 vaccinees not included in these studies in the absence of PBMC samples for assay bridging controls.

Vaccination with rAd35 vectors effectively induced antigen-specific antibody and T-lymphocyte immune responses in either rAd5-naïve or rAd5-immune subjects, suggesting that rare serotype vector genomes are sufficiently distant from common serotypes to resist heterologous vector-directed immunity. This feature of vector performance will be important to circumvent pre-existing immunity stemming not only from natural viral infection, but also from the use of heterologous vectors in priming immunizations or vaccination against other pathogens. Indeed, rAd35-GP inoculation provided a potent boost of both cell-mediated and antibody responses in macaques primed with rAd26-GP. This result was intriguing since it demonstrates a clear difference in vector potency for the induction of secondary versus primary immune responses; the ability of rAd35-GP to boost the immune response was not predicted by the magnitude of responses observed after the priming immunization. These data may indicate that rAd35 and other rAd vectors have a higher transduction efficiency in certain populations or activation states of target dendritic cells, as suggested recently by Lindsay et al., *J Immunol* 185 (3): 1513-21, that may, in this case, be more abundant or accessible during secondary immune responses.

rAd26 proved to be more potent than rAd35 as a single shot vaccine against EBOV infection, mediating survival in up to 75% of vaccinated macaques at the highest dose tested. rAd26-GP vaccines demonstrated a clear dose-response for the induction of protective immunity, suggesting that marginal improvements in antigen expression could increase the potency of rAd26-based vaccines to generated uniform protection against high doses of EBOV challenge, such as those used herein. Interestingly, the higher degree of protection offered by rAd26-GP vectors compared to rAd35-GP at a matched dose ($10^{11}$ particles) associated with higher ELISA anti-GP titers, 1:4500 versus 1:1400, respectively. These data highlight the possibility that prechallenge antibody titers may serve as an immune correlate of protection against ZEBOV infection across rAd serotypes in addition to within vector groups as has been observed for rAd5-GP vaccines. The order of potency for induction of antibody responses predicted the rank order for protection across vector groups.

The studies herein tested vaccine vectors that were compared singly and in combination and demonstrate the utility of alternative serotype rAds for use as vaccine vectors in primates. The results suggest that these vaccines may be most useful in a prime-boost combination.

Because of the high magnitude of antigen-specific responses achieved by heterologous prime-boost, it has been proposed that long term-immunity may be optimally achieved by priming rAd with DNA (Santra, et al., (2005). *J Virol* 79(10): 6516-22). Since DNA requires multiple primes and does not induce rapid protection like rAd vectors do, heterologous rAd prime-boost may provide an optimal opportunity to generate a balance between the induction of rapid, and long lasting protective immunity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing a protective immune response against Ebola in a subject, the method comprising:
administering to the subject, as a priming vaccination, an immunologically effective amount of a recombinant adenovirus vector comprising a polynucleotide encoding a first filovirus antigenic protein, wherein the recombinant adenovirus vector is an rAd26 vector;
followed by administering a boosting vaccination to the subject that includes an adenovirus vector comprising a polynucleotide encoding a second filovirus antigenic protein, wherein the adenovirus vector is an rAd35 vector, so as to induce durable T-cell memory in the subject for the first and second filovirus antigenic proteins and
thus immunizing the subject against Ebola,
wherein each of the first and second filovirus antigenic proteins is a glycoprotein from an Ebola virus; and
wherein, three weeks following the boosting vaccination, the subject has an anti-Ebola glycoprotein EC90 antibody titer of at least 1:32,000.

2. The method according to claim 1, wherein administration is conducted intramuscularly.

3. The method according to claim 1, wherein the Ebola virus is of species *Zaire*.

4. The method according to claim 3, wherein the first and second filovirus antigenic proteins are encoded by SEQ ID NO: 1.

5. The method according to claim 1, wherein the Ebola virus is of species *Sudan/Gulu*.

6. The method according to claim 5, wherein a filovirus antigenic protein is encoded by SEQ ID NO: 2.

7. The method according to claim 5, wherein a filovirus antigenic protein is encoded by SEQ ID NO: 3.

8. A method of inducing immune response protective against death due to infection by Ebola in a subject, the method comprising:
administering to the subject, as a priming vaccination, an immunologically effective amount of a recombinant adenovirus vector comprising a polynucleotide encoding a first antigenic protein encoded by a nucleic acid molecule selected from the group consisting of SEQ ID NO:1, SEQ ID NO: 2, and SEQ ID NO:3, wherein the recombinant adenovirus vector comprises an adenovirus 26 capsid protein;
followed by administering a boosting vaccination to the subject, which includes an adenovirus vector comprising a polynucleotide encoding a second antigenic protein encoded by a nucleic acid molecule selected from the group consisting of SEQ ID NO:1, SEQ ID NO: 2, and SEQ ID NO:3, wherein the adenovirus vector comprises an adenovirus 35 capsid protein.

9. The method according to claim 8, wherein the first and second antigenic proteins are encoded by SEQ ID NO: 1.

10. A method of inducing an immune response protective against death due to infection by Ebola in a subject, the method comprising:
administering to the subject a priming vaccination comprising an E1/E3-deleted rAd26 vector with an Ad5 E4orf6 sequence, the rAd26 vector comprising a polynucleotide encoding a first filovirus antigenic protein; and then
administering to the subject a boosting vaccination comprising an E1/E3-deleted rAd35 vector with an Ad5 E4orf6 sequence, the rAd35 vector comprising a polynucleotide encoding a second filovirus antigenic protein;
so as to induce durable T-cell memory in the subject for the first and second filovirus antigenic proteins and thus protecting the subject against death due to infection by Ebola,
wherein each of the first and second filovirus antigenic proteins is a glycoprotein from an Ebola virus.

11. The method according to claim 10, wherein administration is conducted intramuscularly.

12. The method according to claim 10, wherein the Ebola virus is of species *Zaire*.

13. The method according to claim 12, wherein the first and second filovirus antigenic proteins are encoded by SEQ ID NO: 1.

14. A method of inducing a protective immune response against Ebola in a subject, the method comprising:
administering to the subject, as a priming vaccination, an immunologically effective amount of a recombinant adenovirus vector comprising a polynucleotide encoding a first filovirus antigenic protein, wherein the recombinant adenovirus vector is an rAd26 vector;
followed by administering a boosting vaccination to the subject that includes an adenovirus vector comprising a polynucleotide encoding a second filovirus antigenic protein wherein the adenovirus vector is an rAd35 vector,
so as to induce durable T-cell memory in the subject for the first and second filovirus antigenic proteins and thus immunizing the subject against Ebola,
wherein each of the first and second filovirus antigenic proteins is a glycoprotein from an Ebola virus, and
wherein at least one of the priming vaccination or the boosting vaccination comprises an adjuvant selected from the group consisting of QS-21, Detox-PC, MPL-SE, MoGM-CSF, TiterMax-G, CRL- 1005, GERBU, TERamide, PSC97B, Adjumer, PG-026, GSK-I, GcMAF, B-alethine, MPC-026, Adjuvax, CpG ODN, Betafectin, MF59, lectins, growth factors, cytokines and lymphokines, alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-I0, IL-12, and encoding nucleic acids of any thereof.

15. A method of inducing a protective immune response against Ebola in a subject, the method comprising:
administering to the subject a priming vaccination, the priming vaccination comprising:
an immunologically effective amount of a first recombinant adenovirus vector comprising a polynucleotide encoding a first filovirus antigenic protein, and a immunologically effective amount of a second recombinant adenovirus vector comprising a polynucleotide encoding a second filovirus antigen protein;

wherein the first and second recombinant adenovirus vectors are rAd26 vectors;

followed by administering a boosting vaccination to the subject, the boosting vaccination comprising:

an immunologically effective amount of a third adenovirus vector comprising a polynucleotide encoding the first filovirus antigenic protein, and a immunologically effective amount of a fourth recombinant adenovirus vector comprsing a polynucleotide encoding the second filovirus antigen protein wherein the third and fourth adenovirus vectors are rAd35 vectors, so as to induce durable T-cell memory in the subject for the first and second filovirus antigenic proteins and thus immunizing the subject against Ebola, wherein the first and second filovirus antigenic proteins are glycoproteins from different species of Ebola virus.

* * * * *